US008673301B2

(12) United States Patent
Bonnichsen et al.

(10) Patent No.: US 8,673,301 B2
(45) Date of Patent: Mar. 18, 2014

(54) YKL-40 MONOCLONAL ANTIBODY

(75) Inventors: Richard Bonnichsen, Mahe (SC); Paul Price, La Jolla, CA (US)

(73) Assignees: Bio-Y A/S, Helsingor (DK); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/290,803

(22) Filed: Dec. 2, 2011

(65) Prior Publication Data

US 2012/0149882 A1   Jun. 14, 2012

Related U.S. Application Data

(63) Continuation of application No. 11/817,244, filed as application No. PCT/DK2006/000093 on Feb. 16, 2006, now Pat. No. 8,053,563.

(30) Foreign Application Priority Data

Feb. 28, 2005   (DK) ................. 2005-00300

(51) Int. Cl.
*A61K 39/395*   (2006.01)
(52) U.S. Cl.
USPC ...................................... 424/133.1
(58) Field of Classification Search
None
See application file for complete search history.

(56) References Cited

U.S. PATENT DOCUMENTS

| | | | | |
|---|---|---|---|---|
| 5,935,798 | A * | 8/1999 | Price et al. | 435/7.23 |
| 6,184,204 | B1 * | 2/2001 | Boots et al. | 514/20.6 |
| 7,230,086 | B2 * | 6/2007 | Price et al. | 530/388.1 |
| 8,053,563 | B2 * | 11/2011 | Bonnichsen et al. | 530/387.9 |
| 2005/0214297 | A1 * | 9/2005 | Mao et al. | 424/145.1 |
| 2005/0226884 | A1 | 10/2005 | Price et al. | |

FOREIGN PATENT DOCUMENTS

| WO | WO-95/01995 | 1/1995 |
|---|---|---|
| WO | WO-97/40068 | 10/1997 |
| WO | WO-00/19206 | 4/2000 |

OTHER PUBLICATIONS

Campbell et al Monoclonal Antibody Technology. ed Elseiver p. 1-32 (1984).*
Kharbanda, S. et al., The extracellular matrix proteins, Brevican and Chitinase 3 like 1 (YKL-40) are expressed by distinct subpopulations of glioma, Proc Amer Assoc Cancer Res, 45, 2004, Abstract #1170.
Fusetti Von Moeller, at al., J. bIOL cHEM, 277:25537-44, 2002.
Johansen, J.S., et al., Arthritis Rheum, 44: 826-837, 2001.
Recklies, A.D., et al., Biochem, J. (2002) 365, 119-126.
Baeten, D. et al., Arthritis Rheum, 43: 1233-1243, 2000.
Boot R.G., et al., Arterioscler Thromb Vasc Biol, 19: 687-694, 1999.
XP-002382648, Abstract "Chitinase-3-like protein 1 precursor", (1993) 3 pages.
Jooten, L..A.B., at al., Arthritis & Rheumatism, vol. 43, No. 3, Mar. 2000, pp. 645-655.
Cintin C. et al., Cancer, 95: 267-274, 2002.
Coulson A.F. et al., FEBS Lett, 354:41-4, 1994.
Dasuri, K., Arthritis Res Thor, 6:R161-8,2004.
De Ceunick F., et al., Biochem Biophys Res Commun, 285: 926-931, 2001.
Dehn, H., et al., Acta Obstet Gynaecol Scand, 82: 287-293, 2003.
Dupont J., et al., J Clin Oncol, 22:3330-9, 2004.
Ling, Hua and Recklies, A.D., Biochem. J., (2004) 380, 651-659.
Cintin C., et al., Brit J Cancer, 79:1494-1499, 1999.
Geertsen P., et al., Meeting Proceedings of ASCO 2003:22: abstract 1603.
Gregoire M., et al., Cancer Met Rev, 14: 339-350, 1995.
Harvey S., et al., Clin Chem, 44: 509-516, 1998.
Houston, D.R., et al., J Biol Chem. 278: 30206-30212, 2003.
Huang Y. et al., Proc Natl Acad Sci USA, 98: 15044-15049, 2001.
Hogdall E.V.S. et al., Oncol Rep, 10: 1535-1538, 2003.
Imabayashi H., et al., Exp Cell Res, 288: 35-50, 2003.
Jensen B.V., et al., Clin Cancer Res, 9: 4423-4434, 2003.
Johansen, J.S., et al., J Bone Miner Res, 7: 501-512, 1992.
Johansen, J.S., et al., Br J. Rheumatol, 32: 949-955, 1993.
Johansen, J.S., et al., Eur J. Cancer, 31A: 1437-1442, 1995.
Johansen, J.S., et al., Scand J. Gastroenterol, 32: 582-90, 1997.
Johansen, J.S., et al., Rheumatology, 38: 618-626, 1999b.
Johansen, J.S., et al., Arthritis Rheum, 42: 2624-2630, 1999a.
Brasso K. et al., Meeting proceedings of ASCO 2003; 22: abstract 1525.
Fusetti F. et al., J Biol Chem, 278: 37753-37760, 2003.
Johansen, J.S., et al., Breast Cancer Res Treat, 80: 15-21, 2003.
Johansen, J.S. et al., Lung Cancer, 46: 333-40, 2004.
Junker, N. et al., Cancer Science 2005a, in press.
Junker, N. et al., Lung Cancer 2005b, in press.
Kirkpatrick, R.B., et al., Gene, 153: 147-54, 1995.
Kirkpatrick, R.B., et al., Exp Cell Res, 237: 46-54, 1997.
Koutroubakis, I.E. et al., Int J Colorectal Dis, 18: 287-293, 2003.
Kronborg, G., et al., Scand J Infect Dis, 34: 323-326, 2002.
Malinda, K.M. et al., Exp Cell Res, 250: 168-173, 1999.
Mohanty, A.K., et al., J Biol Chem, 278: 14451-14460, 2003.
Morrison, B.W., et al., Oncogene, 9: 3417-3426, 1994.
Nordenbaek, C., et al., J Infect Dis, 180: 1722-1726, 1999.

(Continued)

*Primary Examiner* — Sheela J Huff
(74) *Attorney, Agent, or Firm* — Gifford, Krass, Sprinkle, Anderson & Citkowski, P.C.

(57) ABSTRACT

The present invention relates to monoclonal anti-human YKL-antibodies which are capable to modulate biological processes in which YKL-40 plays a prominent role, e.g. inhibit the growth and/or inducing apoptosis of cells, in particular cancer cells. The invention also relates to pharmaceutical compositions comprising said antibodies and uses said antibodies and/or pharmaceutical compositions for treatment of a disease wherein inhibition of cell growth, cell differentiation, remodelling of extracellular matrix, metastasis and/or induction of cell death due to apoptosis is a prerequisite for successful curing. An antibody of the invention is capable of inhibiting biological function of YKL-40 in the above mentioned processes by binding to a specific epitope on YKL-40.

7 Claims, 5 Drawing Sheets

(56) References Cited

OTHER PUBLICATIONS

Nishikawa K.C., et al., Exp Cell Res, 287: 79-87, 2003.
Nyirkos P., et al., Biochem J, 269: 265-8, 1990.
Nojgaard C., et al., J Hepatol, 39: 179-186, 2003.
Recklies, A.D., et al., Biochem J, 365: 119-126, 2002.
Rehli M., et al., Genomics, 43: 221-225, 1997.
Rehil M., et al., J Biol Chem, 278: 44058-44068, 2003.
Renkema, G.H., et al., Eur J. Biochem, 251: 504-509, 1998.
Shackel, N.A., et al., Hepatology, 38: 577-88, 2003.
Shackelton, L.M., et al., J Biol Chem, 270: 13076-83, 1995.
Sjogren, H., et al, Am J Pathol, 162: 781-792, 2003.
Sun, Y.J., et al., J Biol Chem 276: 17507-14, 2001.
Tanwar, M.K., et al., Cancer Res, 62: 4364-4368, 2002.
Tran A., et al., Eur J Gastroenterol Hepatol, 12: 989-993, 2000.
Varela P.F., et al., J Biol Chem 277: 13229-36, 2002.
Verhoeckx, K.C., et al., Proteomics, 4: 1014-28, 2004.
Volck, B., et al., Osteoartritis Cartilage, 9: 203-214, 2001.
Volck, B., et al., Proc Assoc Am Phys, 110: 351-360, 1998.
Johansen, J.S., et al., J Hepatol, 32: 911-920, 2000.
Cell Proliferation Assay (AlamarBlue), Sep. 29, 2011, p. 1-3.
Petra Kurek, Therna AW: Frage zzum YKL40 AB AF2599, Sep. 29, 2011, p. 1 of 1.
R & D Systems Tools for Cell Biology Research, Human Chitinase 3-like 1 Antibody p. 1 of 1 Sep. 29, 2011.
Opposition against European Patent No. EP 1 856 153, , Sep. 29, 2011, Bayer Health Care p. 1-13, Sep. 29, 2011.

* cited by examiner

2. LKNRNPNL (SEQ ID NO: 2)
3. VGGWNFGSQR (SEQ ID NO: 3)
4. LAWLYPGRRDK (SEQ ID NO: 4)
5. GAWRGTTGHHS (SEQ ID NO: 5)
6. RGATVHRTLGQ (SEQ ID NO: 6)
7. YATKGNQWVGY (SEQ ID NO: 7)

YKL-40 MONOCLONAL ANTIBODY

CROSS-REFERENCE TO RELATED APPLICATIONS

This application is a continuation of U.S. patent application Ser. No. 11/817,244 filed on Sep. 3, 2008, now U.S. Pat. No. 8,053,563, which is the U.S. national stage of PCT/DK06/00093 filed Feb. 16, 2006, which claims priority of Danish Patent Application PA 2005 00300 filed Feb. 28, 2005.

FIELD OF THE INVENTION

The present invention relates to monoclonal anti-human YKL-40 antibodies, which are capable to inhibit the growth and/or inducing apoptosis of cells, in particular cancer cells, pharmaceutical compositions comprising said antibodies and uses said antibodies and/or pharmaceutical compositions for treatment of a disease wherein inhibition of cell growth, cell differentiation, remodelling of extracellular matrix, metastasis and/or induction of cell death due to apoptosis is a prerequisite for successful curing.

BACKGROUND OF THE INVENTION

YKL-40 was first identified as a protein secreted in large amounts by a human osteosarcoma cell line MG63 in vitro and was named according to the last three N-terminal amino acids of its amino acid sequence, Tyr (Y), Lys (K) and Leu (L), and approximate molecular weight of 40 kDa (Johansen et al., 1992).

Analysis of the amino acid sequence of YKL-40 revealed that the protein belongs to the glycosyl hydrolase family 18 (Hakala et al., 1993). The family consists of enzymes including chitinases and also proteins, which do not have enzymatic activity. The gene for YKL-40 (CHI3L1) is located on chromosome 1q31-1q32 and consists of 10 exons and spans about 8 kilobases of genomic DNA (Rehli et al., 1997). The Sp1-family transcription factors seem to have a predominantly role in controlling YKL-40 promoter activity (Rehi et al., 2003). The crystallographic structure of human YKL-40 has been described (Fusetti et al., 2003; Houston et al., 2003). The protein contains two globular domains: a big core domain which consists of a $(\beta/\alpha)_8$ domain structure with a triose-phosphate isomerase (TIM) barrel fold, and a small $\alpha/\beta$ domain, composed of five antiparallel β-strands and one α-helix, inserted in the loop between strand β7 and helix α7. This confers to the active site of YKL-40 a groove-like character. The structure of YKL-40 is in part similar to the structure of several proteins, e.g. human chitotriosidase (Fusetti et al., 2002), mouse Ym1 (Sun et al., 2001), *Drosophila melanogaster* imaginal disc growth factor-2 (Varela et al., 2002) and some other members of the glycosyl hydrolase family 18 (Coulson, 1994), but there are also major differences. One of these differences is a mutation of one of the three amino acids (Asp, Glu and Asp) essential for the chitinase-like catalytic activity, namely Glu->Leu, which completely rules out the function of YKL-40 as a glycolytic enzyme. YKL-40 can binds chitin, but has no enzymatic activity (Renkema et al., 1998). YKL-40 is a glycoprotein and this is also a unique feature of YKL-40 comparing to the other mammalian chitinase-like proteins.

YKL-40 can bind heparin. The amino acid sequence of the protein contains one heparin binding motif ($^{143}$GRRD-KQH$^{149}$) which is located in a surface loop (Fusetti et al., 2003). YKL-40 can also bind hyaluronan. The folded protein contains two potential hyaluronan binding sites on the external face. Human YKL-40 can bind chitin of different lengths in a similar fashion as chitinases of the Family 18. Nine sugar-binding subsites were identified in the 43 Å groove of YKL-40 (Fusetti et al., 2003). Binding of short or long oligosaccharides to human YKL-40 is also possible. The presence of two distinct binding sites with selective affinity for long and short oligosaccharides (not found in other mammalian chitinase-like proteins) may have significance for the functional activity of YKL-40 as a cross-linker between two targets carrying these oligosaccharides.

YKL-40 possesses a number of biological activities. Thus, it has been shown that human YKL-40 can act as a growth factor for cells of connective tissue, such as chondrocytes and synovial cells (De Ceuninck et al., 2001; Recklies et al., 2002). YKL-40 also promotes the growth of fibroblasts in a fashion similar to insulin-like growth factor 1 (IGF-1) (Recklies et al., 2002). In fibroblasts YKL-40 initiates activation of MAP kinase and PI3K signalling cascades leading to phosphorylation of both the extracellular signal-regulated kinase (ERK)-1/2 MAP kinase and protein kinase B (AKT). Activation of cytoplasmic signal-transduction pathways by YKL-40 has been suggested to be mediated through interaction of YKL-40 with one or more receptor molecules on the plasma membrane, but the identity of the cellular receptor mediating the biological effects of YKL-40 is currently unknown.

It has also been demonstrated that YKL-40 acts as a chemoattractant for endothelial cells and stimulates migration of these cells comparable to stimulation by basic fibroblast growth factor (Malinda et al., 1999).

YKL-40 modulates vascular endothelial cell morphology by promoting the formation of branching tubules, indicating that YKL-40 may play a role in angiogenesis by stimulating the migration and reorganization of vascular endothelial cells (Malinda et al., 1999). YKL-40 is also an adhesion and migration factor for vascular smooth muscle cells (Nishikawa et al., 2003). It has been suggested that YKL-40 may affect the local extracellular hyaluronan concentrations available for cell attachment via two independent mechanisms: by binding to the extracellular hyaluronan, and by interfering with the synthesis and secretion of hyaluronan by cells. Thus, YKL-40 may influence the extent of cell adhesion and migration during the tissue remodeling processes that take place during inflammation, fibrosis, atherogenesis and cancer growth and cancer metastasis.

In mice YKL-40 was called the "breast regression protein (Brp-39)" because the expression of the protein was induced in mammary epithelial cells a few days after weaning. It was proposed (Mohanty et al., 2003) that YKL-40 is involved in regulation of programmed cell death during mammary involution as a protective signalling factor that determines which cells are to survive the drastic tissue remodelling that occurs during involution.

YKL-40 is expressed by different types of cells in vitro and in vivo, in particular in tissues characterised by inflammation, degradation/remodeling of the extracellular matrix or ongoing fibrogenesis. YKL-40 is secreted by activated neutrophils (Volck et al., 1998), by macrophages during late state of differentiation (Kirckpatrick et al., 1997; Krause et al. 1996; Rehli et al., 1997; Renkema et al., 1998; Rehli et al., 2003), arthritic chondrocytes (Hakala et al., 1993; Johansen et al. 2001; Volck et al. 2001), differentiated vascular smooth muscle cells (Shackelton et al., 1995; Malinda et al., 1999; Nishikawa et al. 2003) and fibroblast-like synovial cells (Hakala et al. 1993; Nyirkos et al., 1990; Dasuri et al, 2004). Studies in human fetal chondrocytes indicate that YKL-40 is a differentiation marker (Imabayashi et al., 2003). In vivo YKL-40 mRNA and proteins expression are found by a subpopulation of macrophages in inflamed synovial membrane (Kirkpatrick et al., 1997; Baeten et al., 2000; Volck et al., 2001), atheromatous plaques (Boot et al. 1999), arteritic vessels from patients with giant cell arteritis (Johansen et al., 1999a) and by arthritic chondrocytes (Volck et al., 2001), and peritumoral macrophages in biopsies from small cell lung cancer express YKL-40 mRNA (Junker et al., 2005b).

A strong expression of YKL-40 mRNA in human liver has been shown to be associated with the presence of fibrosis. Immunohistochemical studies of liver biopsies have shown YKL-40 protein expression in areas of the liver with fibrosis, whereas no expression was observed in hepatocytes (Johansen et al., 1997; Johansen et al. 2000). Suppression subtractive hybridization analysis and RT-PCR have demonstrated that YKL-40 is one of the most overexpressed proteins in cirrhotic liver tissue caused by hepatitis C virus (HCV) (Shackel et al., 2003).

Patients with non-malignant diseases characterized by inflammation and fibrosis such as active rheumatoid arthritis (Johansen et al., 1993; Harvey et al., 1998; Johansen et al., 1999b; Volck et al., 2001), severe bacterial infections (Nordenbaek et al., 1999; Kronborg et al., 2002), active inflammatory bowel disease (Koutroubakis et al., 2003; Vind et al., 2003), and liver fibrosis (Johansen et al., 1997; Johansen et al., 2000; Tran et al., 2000; Nojgaard et al., 2003) have elevated serum YKL-40.

YKL-40 is expressed and secreted by several types of human carcinoma (breast, colon, lung, kidney, ovarian, prostate, uterine, osteosarcoma, oligodendroglioma, glioblastoma and germ cell tumors) (A search of the YKL-40 sequence against the dbest database at the National Center for Biotechnology Information; Johansen et al., 1992; Junker et al., 2005a), and by murine mammary tumors initiated by neu/ras oncogenes (Morrison et al., 1994). Microarray gene analyses have identified the YKL-40 gene as one of the most overexpressed genes in papillary thyroid carcinoma (Huang et al., 2001), high-grade malignant gliomas (Tanwar et al., 2002), and extracellular myxoid chondrosarcoma (Sjogren et al., 2003). YKL-40 is expressed and secreted in vitro by the osteosarcoma cell line MG63, glioblastoma cells and myeloid leukemia cell lines (U937, THP-1, HL-60) (Johansen et al., 1992; Rehli et al., 2003; Kirkpatrick et al., 1995; Verhoeckx et al., 2004). YKL-40 is not expressed by small cell lung cancer cell lines in vitro nor in vivo but strongly expressed by tumor associated macrophages in small cell lung cancer biopsies (Junker et al., 2005b).

A number of studies has now reported an elevated level of YKL-40 protein in serum of cancer patients (Johansen et al., 1995; Cintin et al., 1999; Cintin et al., 2002; Tanwar et al., 2002; Brasso et al., 2003; Dehn et al., 2003; Geertsen et al., 2003; Hogdall et al., 2003; Jensen et al., 2003; Johansen et al., 2003; Dupont et al., 2004; Johansen et al., 2004). Several studies have demonstrated that an elevated serum concentration of YKL-40 in patients with breast-, colorectal-, ovarian-, kidney-, small cell lung-, and prostate carcinomas is an independent prognostic parameter of short recurrence free interval and short overall survival. This observation has been done in patients with local or advanced cancer at time of first cancer diagnosis and at time of relapse (Johansen et al., 1995; Cintin et al., 1999; Cintin et al., 2002; Brasso et al., 2003; Dehn et al., 2003; Geertsen et al., 2003; Hogdall et al., 2003; Jensen et al., 2003; Johansen et al., 2003; Dupont et al., 2004; Johansen et al., 2004). Based on these and other findings YKL-40 was suggested as a diagnostic marker of the presence or absence of a cancer and for the prognosis of cancer recurrence and survival of cancer patients (WO 00/19206), and it was described as a marker for degradation of connective tissue and used in methods for identifying the presence of a disease associated with degradation of connective tissue (e.g. cancer) described (WO 95/01995; U.S. Pat. No. 5,935,798). Both groups of latter methods are based on employing an anti-YKL-40 antibody for detecting the protein in samples from the patients.

Antibodies against YKL-40 has long been known in the art and used for example for the detection and monitoring the level of YKL-40 in blood serum/plasma of cancer patients, however, functional anti-YKL-40 antibodies, which would be capable of inhibiting the function of YKL-40, have not been produced nor described.

REFERENCES

Baeten D, Boots A M H, Steenbakkers P G A, Elewaut D, Bos E, Verheijden G F M, Verbruggen G, Miltenburg A M M, Rijnders A W M, Veys E M, De Keyser F. Human cartilage gp-39+, CD16+ monocytes in peripheral blood and synovium. Correlation with joint destruction in rheumatoid arthritis. Arthritis Rheum, 43: 1233-1243, 2000.

Boot R G, van Achterberg T A E, van Aken B E, Renkema G H, Jacobs M J H M, Aerts J M F G, de Vries C J M. Strong induction of members of the chitinase family of proteins in atherosclerosis. Chitotriosidase and human cartilage gp-39 expressed in lesion macrophages. Arterioscler Thromb Vasc Biol, 19: 687-694, 1999.

Brasso K, Johansen J S, Christensen I J, Teisner B, Price P A, Iversen P. High serum levels of PINP, bone alkaline phosphatase and YKL-40 in patients with advanced prostate carcinoma are associated with short survival. Meeting Proceedings of ASCO 2003; 22:abstract 1525.

Cintin C, Johansen J S, Christensen I J, Price P A, Sorensen S, Nielsen H J. Serum YKL-40 and colorectal cancer. Brit J Cancer, 79:1494-1499, 1999.

Cintin C, Johansen J S, Christensen I J, Price P A, Sorensen S, Nielsen H J. High serum YKL-40 level after surgery for colorectal carcinoma is related to short survival. Cancer, 95: 267-274, 2002.

Coulson A F. A proposed structure for 'family 18' chitinases. A possible function for narbonin. FEBS Lett, 354:41-4, 1994.

Dasuri K, Antonovici M, Chen K, Wong K, Standing K, Ens W, El-Gabalawy H, Wilkins J A. The synovial proteome: analysis of fibroblast-like synoviocytes. Arthritis Res Ther, 6:R161-8, 2004.

De Ceuninck F, Gaufillier S, Bonnaud A, Sabatini M, Lesur C, Pastoureau P. YKL-40 (cartilage gp-39) induces proliferative events in cultured chondrocytes and synoviocytes and increases glycosaminoglycan synthesis in chondrocytes. Biochem Biophys Res Commun, 285: 926-931, 2001.

Dehn H, Hogdall E V S, Johansen J S, Price P A, Jorgensen M, Engelholm S M, Hogdall C K. Plasma YKL-40, as a prognostic tumor marker in recurrent ovarian cancer. Acta Obstet Gynaecol Scand, 82: 287-293, 2003.

Dupont J, Tanwar M K, Thaler H T, Fleisher M, Kauff N, Hensley M L, Sabbatini P, Anderson S, Aghajanian C, Holland E C, Spriggs D R. Early detection and prognosis of ovarian cancer using serum YKL-40. J Clin Oncol, 22:3330-9, 2004.

Fusetti von Moeller H, Houston D, Rozeboom H J, Dijkstra B W, Boot R G, Aerts J M, van Aalten D M. Structure of human chitotriosidase. Implications for specific inhibitor design and function of mammalian chitinase-like lectins. J Biol Chem, 277:25537-44, 2002

Fusetti F, Pijning T, Kalk K H, Bos E, Dijkstra B W. Crystal structure and carbohydrate binding properties of the human cartilage glycoprotein-39. J Biol Chem, 278: 37753-37760, 2003.

Geertsen P, Johansen J S, von der Maase H, Jensen B V, Price P A. High pretreatment serum level of YKL-40 is related to short survival in patients with advanced renal cell carcinoma treated with high-dose continuous intravenous infusion of interleukin-2. Meeting Proceedings of ASCO 2003; 22: abstract 1603.

Gregoire M, Lieubeau B. The role of fibroblasts in tumor behavior. Cancer Met Rev, 14: 339-350, 1995.

Harvey S, Weisman M, O'Dell J, Scott T, Krusemeier M, Visor J, Swindlehurst C. Chondrex: new marker of joint disease. Clin Chem, 44: 509-516, 1998.

Houston D R, Recklies A D, Krupa J C, van Aalten D M F. Structure and ligand-induced conformational change of the 39-kDa glycoprotein from human articular chondrocytes. J Biol Chem, 278: 30206-30212, 2003.

Huang Y, Prasad M, Lemon W J, Hampel H, Wright F A, Kornacker K, LiVolsi V, Frankel W, Kloos R T, Eng C, Pellegata N S, de la Chapelle A. Gene expression in papillary thyroid carcinoma reveals highly consistent profiles. Proc Natl Acad Sci USA, 98:15044-15049, 2001.

Hogdall E V S, Johansen J S, Kjaer S K, Price P A, Christensen L, Blaakaer J, Bock J E, Glud E, Hogdall C K. High plasma YKL-40 level in patients with ovarian cancer stage III is related to shorter survival. Oncol Rep, 10: 1535-1538, 2003.

Imabayashi H, Mori T, Gojo S, Kiyono T, Sugiyama T, Irie R, Isogai T, Hata J, Toyama Y, Umezawa A. Redifferentiation of dedifferentiated chondrocytes and chondrogenesis of human bone marrow stromal cells via chondrosphere formation with expression profiling by large-scale cDNA analysis. Exp Cell Res, 288:35-50, 2003.

Jensen B V, Johansen J S, Price P A. High levels of serum HER-2/neu and YKL-40 independently reflect aggressiveness of metastatic breast cancer. Clin Cancer Res, 9: 501-512, 2003.

Johansen J S, Williamson M K, Rice J S, Price P A. Identification of proteins secreted by human osteoblastic cells in culture. J Bone Miner Res, 7: 501-512, 1992.

Johansen J S, Jensen H S, Price P A. A new biochemical marker for joint injury. Analysis of YKL-40 in serum and synovial fluid. Br J Rheumatol, 32: 949-955, 1993.

Johansen J S, Cintin C, Jorgensen M, Kamby C, Price P A. Serum YKL-40: a new potential marker of prognosis and location of metastases of patients with recurrent breast cancer. Eur J Cancer, 31A: 1437-1442, 1995.

Johansen J S, Moller S, Price P A, Bendtsen F, Junge J, Garbarsch C, Henriksen J H. Plasma YKL-40: a new potential marker of fibrosis in patients with alcoholic cirrhosis? Scand J Gastroenterol, 32: 582-90, 1997.

Johansen J S, Baslund B, Garbarsch C, Hansen M, Stoltenberg M, Lorenzen I, Price P A. YKL-40 in giant cells and macrophages from patients with giant cell arteritis. Artritis Rheum, 42: 2624-2630, 1999a.

Johansen J S, Stoltenberg M, Hansen M, Florescu A, Horslev-Petersen K, Lorenzen I, Price P A. Serum YKL-40 concentrations in patients with rheumatoid arthritis: relation to disease activity. Rheumatology, 38: 618-626, 1999b.

Johansen J S, Christoffersen P, Moller S, Price P A, Henriksen J H, Garbarsch C, Bendtsen F. Serum YKL-40 is increased in patients with hepatic fibrosis. J Hepatol, 32: 911-920, 2000.

Johansen J S, Olee T, Price P A, Hashimoto S, Ochs R L, Lotz M. Regulation of YKL-40 production by human articular chondrocytes. Arthritis Rheum, 44: 826-837, 2001.

Johansen J S, Christensen I J, Riisbro R, Greenall M, Han C, Price P A, Smith K, Brunner N, Harris A L. High serum YKL-40 levels in patients with primary breast cancer is related to short recurrence free survival. Breast Cancer Res Treat, 80: 15-21, 2003.

Johansen J S, Drivsholm L, Price P A, Christensen I J. High serum YKL-40 level in patients with small cell lung cancer is related to early death. Lung Cancer, 46:333-40, 2004.

Junker N, Johansen J S, Hansen L T, Lund E L, Kristjansen P E G. Differential regulation of YKL-40 during genotoxic or microenvironmental stress in three human glioblastoma cell lines. Cancer Science 2005a, in press.

Junker N, Johansen J S, Andersen C B, Kristjansen P E G. Expression of YKL-40 by peritumoral macrophages in human small cell lung cancer. Lung Cancer 2005b, in press.

Kirkpatrick R B, Matico R E, McNulty D E, Strickler J E, Rosenberg M. An abundantly secreted glycoprotein from *Drosophila melanogaster* is related to mammalian secretory proteins produced in rheumatoid tissues and by activated macrophages. Gene, 153:147-54, 1995.

Kirkpatrick R B, Emery J G, Connor J R, Dodds R, Lysko P G, Rosenberg M. Induction and expression of human cartilage glycoprotein 39 in rheumatoid inflammatory and peripheral blood monocyte-derived macrophages. Exp Cell Res, 237:46-54, 1997.

Koutroubakis I E, Petinaki E, Dimoulios P, Vardas E, Roussomoustakaki M, Maniatis A N, Kouroumalis E A. Increased serum levels of YKL-40 in patients with inflammatory bowel disease. Int J Colorectal Dis, 18:287-293, 2003.

Kronborg G, Ostergaard C, Weis N, Nielsen H, Obel N, Pedersen S S, Price P A, Johansen J S. Serum level of YKL-40 is elevated in patients with *Streptococcus pneumoniae* bacteremia and is associated to the outcome of the disease. Scand J Infect Dis, 34:323-326, 2002.

Malinda K M, Ponce L, Kleinman H K, Shackelton L M, Millis A J T. Gp38k, a protein synthesized by vascular smooth muscle cells, stimulates directional migration of human umbilical vein endothelial cells. Exp Cell Res, 250: 168-173, 1999.

Mohanty A K, Singh G, Paramasivam M, Saravanan K, Jabeen T, Sharma S, Yadav S, Kaur P, Kumar P, Srinivasan A, Singh T P. Crystal structure of a novel regulatory 40 kDa mammary gland protein (MGP-40) secreted during involution. J Biol Chem, 278: 14451-14460, 2003.

Morrison B W and Leder P. neu and ras initiate murine mammary tumors that share genetic markers generally absent in c-myc and int-2-initiated tumors. Oncogene, 9: 3417-3426, 1994.

Nordenbaek C, Johansen J S, Junker P, Borregaard N, Sorensen O and Price P A. YKL-40, a matrix protein of specific granules in neutrophils, is elevated in serum of patients with community-acquired pneumonia requiring hospitalization. J Infect Dis, 180: 1722-1726, 1999.

Nishikawa K C, Millis A J T. gp38k (CHI3L1) is a novel adhesion and migration factor for vascular cells. Exp Cell Res, 287: 79-87, 2003.

Nyirkos P, Golds E E. Human synovial cells secrete a 39 kDa protein similar to a bovine mammary protein expressed during the non-lactating period. Biochem J, 269:265-8, 1990.

Nojgaard C, Johansen J S, Christensen E, Skovgaard L T, Price P A, Becker U and The EMALD Group. Serum levels of YKL-40 and PIIINP as prognostic markers in patients with alcoholic liver disease. J Hepatol, 39: 179-186, 2003.

Recklies A D, White C, Ling H. The chitinase 3-like protein human cartilage 39 (HC-gp39) stimulates proliferation of human connective-tissue cells and activates both extracellular signal-regulated kinase- and protein kinase B-mediated signalling pathways. Biochem J, 365: 119-126, 2002.

Rehli M, Krause S W, Andreesen R. Molecular characterization of the gene for human cartilage gp-39 (CHI3L1), a member of the chitinase protein family and marker for late stages of macrophage differentiation. Genomics, 43: 221-225, 1997.

Rehli M, Niller H-H, Ammon C, Langmann S, Schwarzfischer L, Andreesen R, Krause S W. Transcriptional regulation of CHI3L1, a marker gene for late stages of macrophage differentiation. J Biol Chem, 278: 44058-44068, 2003.

Renkema G H, Boot G R, Au F L, Donker-Koopman W E, Strijland A, Muijsers A O, Hrebicek M, Aerts JMFG. Chitotriosidase, a chitinase, and the 39-kDa human cartilage glycoprotein, a chitin-binding lectin, are homologues of family 18 glycosyl hydrolases secreted by human macrophages. Eur J Biochem, 251: 504-509, 1998.

Shackel N A, McGuinness P H, Abbott C A, Gorrell M D, McCaughan G W. Novel differential gene expression in human cirrhosis detected by suppression subtractive hybridization. Hepatology, 38:577-88, 2003.

Shackelton L M, Mann D M, Millis A J. Identification of a 38-kDa heparin-binding glycoprotein (gp38k) in differentiating vascular smooth muscle cells as a member of a group of proteins associated with tissue remodeling. J Biol Chem, 270:13076-83, 1995.

Sjogren H, Meis-Kindblom J M, Orndal C, Bergh P, Ptaszynski K, Aman P, Kindblom L G, Stenman G. Studies on the molecular pathogenesis of extraskeletal myxoid chondrosarcoma-cytogenetic, molecular genetic, and cDNA microarray analyses. Am J Pathol, 162: 781-792, 2003.

Sun Y J, Chang N C, Hung S I, Chang A C, Chou C C, Hsiao C D. The crystal structure of a novel mammalian lectin, Ym1, suggests a saccharide binding site. J Biol Chem 276:17507-14, 2001.

Tanwar M K, Gilbert M R, Holland E C. Gene expression microarray analysis reveals YKL-40 to be a potential serum marker for malignant character in human glioma. Cancer Res, 62: 4364-4368, 2002.

Tran A, Benzaken S, Saint-Paul M-C, Guzman-Granier E, Hastier P, Pradier C, Barjoan E M, Demuth N, Longo F, Rampal P. Chondrex (YKL-40), a potential new serum fibrosis marker in patients with alcoholic liver disease. Eur J Gastroenterol Hepatol, 12: 989-993, 2000.

Varela P F, Llera A S, Mariuzza R A, Tormo J. Crystal structure of imaginal disc growth factor-2. A member of a new family of growth-promoting glycoproteins from *Drosophila melanogaster*. J Biol Chem 277:13229-36, 2002.

Verhoeckx K C, Bijisma S, de Groene E M, Witkamp R F, van der Greef J, Rodenburg R J. A combination of proteomics, principal component analysis and transcriptomics is a powerful tool for the identification of biomarkers for macrophage maturation in the U937 cell line. Proteomics, 4:1014-28, 2004.

Volck B, Johansen J S, Stoltenberg M, Garbarsch C, Price P A, Ostergaard M, Ostergaard K, Lovgreen-Nielsen P, Sonne-Holm S, Lorenzen I. Studies on YKL-40 in knee joints of patients with rheumatoid arthritis and osteoarthritis. Involvement of YKL-40 in the joint pathology. Osteoarthritis Cartilage, 9: 203-214, 2001.

Volck B, Price P A, Johansen J S, Sorensen O, Benfield T L, Nielsen H J, Calafat J, Borregaard N. YKL-40, a mammalian member of the chitinase family, is a matrix protein of specific granules in human neutrophils. Proc Assoc Am Phys, 110: 351-360, 1998.

SUMMARY OF THE INVENTION

The present invention relates to a finding that monoclonal antibodies against human YKL-40 are able to significantly inhibit cell growth, cell differentiation, cell survival and metastasis.

Thus, in one aspect the present invention relates to a monoclonal anti-human YKL-40 antibody, antigen binding fragment or recombinant protein thereof, said antibody, binding fragment or recombinant protein thereof being capable of
  inhibiting cell growth, such as e.g. endothelial, fibroblast, synoviocytes, chondrocyte, hepatic stellate cells, vascular smooth muscle cells, monocyte/macrophage or cancer cell growth, and/or
  inducing cell death, such as e.g. endothelial, fibroblast, synoviocytes, chondrocyte, hepatic stellate cells, vascular smooth muscle cells, monocyte/macrophage or cancer cell death, and/or
  inhibiting cell differentiation, such as e.g. endothelial, fibroblast, synoviocytes, chondrocyte, hepatic stellate cells, vascular smooth muscle cell, monocyte/macrophage or cancer cell differentiation, and/or
  inhibiting cancer cell metastatic potential.

A monoclonal anti-human YKL-40 antibody according to the invention is capable to inhibit functional activity of human YKL-40 associated with cell growth, differentiation, survival and extracellular tissue remodeling. In particular, the invention relates to an antibody which is capable of inhibiting biological activity of YKL-40 in
  development/progression of cancer cell growth, and/or
  development/progression of cancer cell metastasis, and/or
  development/progression of cancer cell differentiation, and/or
  development/progression of cancer cell survival, and/or
  development/progression of angiogenesis, and/or
  development/progression of extracellular matrix remodeling, and/or
  development/progression of liver fibrosis, and/or
  development/progression of lung fibrosis, and/or
  development/progression of tissue fibrosis, and/or
  development/progression of organ fibrosis, and/or
  development/progression of rheumatoid arthritis.

The invention features an antibody which is capable of inhibiting biological function of YKL-40 in the above mentioned processes upon binding to a specific epitope on YKL-40.

The invention, thus, in further aspects relates to an epitope recognizable by the above antibodies. The epitope of the invention is characterised in that it comprises amino acid residues of any of the sequences identified herein as SEQ ID NOs: 2, 3, 4, 5, 6, or 7, or consists of at least one of said sequences or a fragment thereof. According to the invention said epitope is a binding site, constitutes a part of a binding site of YKL-40 to its receptor, Or is involved in assisting the activation of the receptor by YKL-40 by interacting with some other molecules, for example an YKL-40 ligand, such as for example heparin, heparan sulfate proteoglycans, or hyaluronan.

Use of an antibody capable of recognizing the epitope as defined above for the
  i) inhibiting cell growth (including cancer) and/or
  ii) inhibiting cell differentiation (including cancer) and/or
  iii) inhibiting cell survival (including cancer) and/or iv) inducing cell death (including cancer) and/or
v) inhibiting development/progression of extracellular matrix remodeling, and/or
vi) inhibiting development/progression of liver fibrosis, and/or
vii) inhibiting development/progression of rheumatoid arthritis, and/or
viii) inhibiting development/progression of organ fibrosis, and/or
ix) inhibiting development/progression of tissue fibrosis, and/or
x) inhibiting development/progression of angiogenesis, and/or
xi) inhibiting metastasis is also an aspect of the invention. The invention in particular features uses of the antibodies for the treatment of cancer and/or non-malignant diseases, such as for example inflammatory diseases and diseases associated with fibrosis.

The invention also relates to a pharmaceutical composition comprising the above antibody, antigen binding fragment or recombinant protein thereof.

The invention also relates to peptide sequences comprising or being comprised by the epitope for the
i) production of an antibody of the invention, and/or
ii) modulating functional activity of YKL-40 receptor associated with cell proliferation, differentiation and survival, and/or
iii) modulating biological functions of YKL-40, and/or
iv) manufacture of a medicament.

The invention concerns pharmaceutical compositions comprising the antibodies and/or peptide sequences as defined above as well.

DETAILED DESCRIPTION OF THE INVENTION

Antibody

Figure 1:
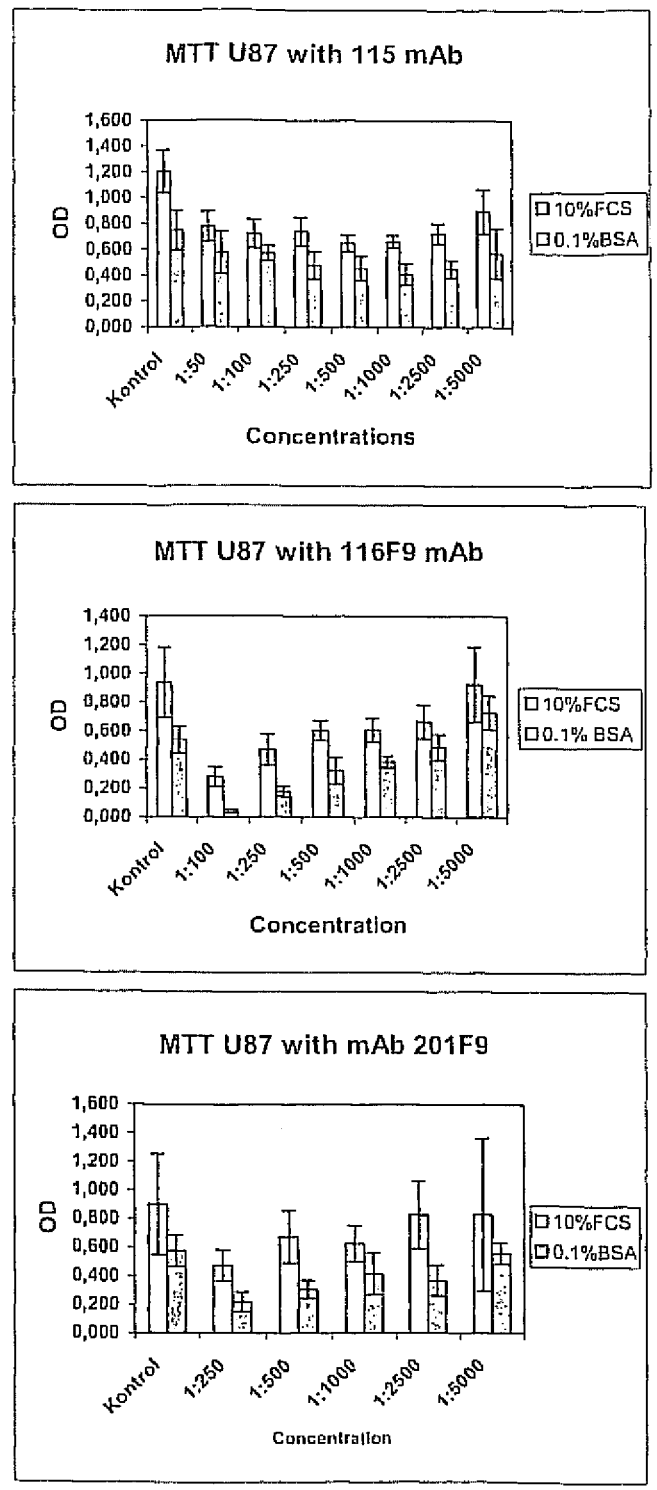
FIG. 1 shows the effect of different monoclonal antibodies against human YKL-40 (mAb 115F9, 116F9 and 201F9) on cell growth and survival of malignant human glioblastoma U87 cells in vitro (MTT assay). Results are given as the mean value of 6 measurements+/−standard deviation.

It is an objective of the present invention to provide an antibody, antigen binding fragment or recombinant protein thereof capable of recognizing and selectively binding to an epitope on human YKL-40 comprising at least one of the sequences selected from SEQ ID NOs:2-7 and thereby inhibiting biological activity of YKL-40 associated with cell growth, cell differentiation, cell survival, and extracellular tissue remodeling processes.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Novotny J, & Haber E. Proc Natl Acad Sci USA. 82(14):4592-6, 1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab').sub.2 and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an $F(ab')_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and $F(ab')_2$ fragments.

The term "antibody fragment" is used herein interchangeably with the term "antigen binding fragment".

Antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it is has similar or immunological properties relative to antibody that binds with specificity to an epitope comprising of amino acid residues 83-90, 96-105, 137-150, 210-220, 304-314 and/or 318-329 of the SEQ ID NO: 1, or a peptide sequence selected from any of the sequences identified herein as SEQ ID NOs: 2-7, or a fragment of said sequences. Thus, in context of the present invention the term "antibody fragment" is identical to term "antigen binding fragment".

Antibody fragments retain some ability to selectively bind with its antigen or receptor. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

(3) $(Fab')_2$ is the fragment of an antibody that can be obtained by treating whole antibody with the enzyme pepsin without subsequent reduction.

(4) F(ab')2 is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies 113: 269-315 Rosenburg and Moore eds. Springer-Verlag, NY, 1994.

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444-6448 (1993).

The invention contemplate both polyclonal and monoclonal antibody against human YKL-40, antigen binding fragments and recombinant proteins thereof which possess at least one functional activity according to the invention.

The preparation of polyclonal antibodies is well-known to those skilled in the art. See, for example, Green et al. 1992. Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1, which are hereby incorporated by reference.

The preparation of monoclonal antibodies likewise is conventional. See, for example, Kohler & Milstein, Nature, 256: 495-7 (1975); Coligan, et al., sections 2.5.1-2.6.7; and Harlow, et al., in: Antibodies: A Laboratory Manual, page 726, Cold Spring Harbor Pub. (1988), Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG). In: Methods in Molecular Biology, 1992, 10:79-104, Humana Press, NY.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies for use with the present invention may also be isolated from phage antibody libraries using the techniques described in Clackson et al., 1991, Nature 352: 624-628, as well as in Marks et al., 1991, J Mol Biol 222: 581-597. Another method involves humanizing a monoclonal antibody by recombinant means to generate antibodies containing human specific and recognizable sequences. See, for review, Holmes, et al., 1997, J Immunol 158:2192-2201 and Vaswani, et al., 1998, Annals Allergy, Asthma & Immunol 81:105-115.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al., 1984, Proc Natl Acad Sci 81: 6851-6855.

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in $E.$ $coli$ of DNA encoding the fragment. Antibody fragments can be obtained by pepsin or papain digestion of whole antibodies conventional methods. For example, antibody fragments can be produced by enzymatic cleavage of antibodies with pepsin to provide a 5 S fragment denoted $F(ab')_2$. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab' fragments and an Fc fragment directly. These methods are described, for example, in U.S. Pat. Nos. 4,036,945 and 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as $E.$ $coli$. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988, Science 242:423-426; U.S. Pat. No. 4,946,778; and Pack, et al., 1993, BioTechnology 11:1271-77.

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', $F(ab')_2$ or other antigen-binding subsequences of antibodies) that contain a minimal sequence derived from non-human immunoglobulin, such as the epitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es) of the invention, such as a sequence(s) recognising the epitope(s) described herein, is a preferred embodiment of the invention. In particular, the invention relates to humanized forms of mouse anti-human YKL-40 monoclonal antibodies 201F9 and 116F9.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., 1986, Nature 321, 522-525; Reichmann et al., 1988, Nature 332, 323-329; Presta, 1992, Curr Op Struct Biol 2:593-596; Holmes et al., 1997, J Immunol 158:2192-2201 and Vaswani, et al., 1998, Annals Allergy, Asthma & Immunol 81:105-115.

The generation of antibodies may be achieved by any standard methods in the art for producing polyclonal and monoclonal antibodies using a natural or recombinant human YKL-40 polypeptide or fragments thereof as an antigen. Such antibodies would be in a preferred embodiment generated using a naturally occurring or recombinantly produced human YKL-40 (Swissprot Ass. No.: P36222) identified herein as SEQ ID NO: 1, or variants or fragments thereof, or, in a more preferred embodiment, using fragments of said polypeptides, said fragments being immunogenic fragments which meet at least two of the following criteria:
  (i) being a contiguous amino acid sequence of at least 5 amino acids;
  (ii) comprising an amino acid sequence derived from the sequence identified as SEQ ID NO: 1 or
  (iii) comprising an amino acid sequence identified in SEQ ID NOs: 2-7, or a fragment thereof.

The antibodies may also be produced in vivo by the individual to be treated, for example, by administering an immunogenic fragment according to the invention to said individual. Accordingly, the present invention further relates to a vaccine comprising an immunogenic fragment described above.

The application also relates to a method for producing an antibody of the invention said method comprising a step of providing of YKL-40 or an immunogenic fragment of YKL-40 described herein.

The invention relates to an antibody, which is capable of inhibiting biological function of YKL-40 in connection with cell growth, differentiation, survival, metastatic potential and tissue remodeling, such as e.g. extracellular matrix remodelling with development of fibrosis. In one embodiment such antibody may be an anti-human YKL-40 antibody, or antibody fragment, or recombinant protein thereof, which is capable of binding to an epitope comprising amino acid residues 83-90, 96-105, 137-150, 210-220, 304-314 and/or 318-329 of the SEQ ID NO: 1, or a sequence selected from SEQ ID NOs: 2-7, or a fragment of said sequences. Preferably, the epitope is located within the sequence YKL-40 (SEQ ID NO: 1)

In another embodiment the invention relates to an antibody, which is not an anti-human YKL-40 antibody, said antibody being capable of recognising and binding to the epitope, which is recognised by anti-human YKL-40 antibody of above.

In still another embodiment the invention relates to a non-antibody compound, which is capable of binding to the epitope described herein and thereby inhibiting the function of YKL-40 protein in association with
  development/progression of cancer growth, and/or
  development/progression of cancer differentiation, and/or
  development/progression of cancer survival, and/or
  development/progression of cancer metastasis, and/or
  development/progression of angiogenesis, and/or
  development/progression of extracellular matrix remodeling, and/or
  development/progression of liver fibrosis, and/or
  development/progression of lung fibrosis, and/or
  development/progression of tissue fibrosis, and/or
  development/progression of organ fibrosis, and/or
  development of rheumatoid arthritis.

By the term "epitope" is meant the specific group of atoms (on an antigen molecule) that is recognized by (that antigen's) antibodies (thereby causing an immune response). The term "epitope" is the equivalent to the term "antigenic determinant" The epitope may comprise 3 or more amino acid residues, such as for example 4, 5, 6, 7, 8 amino acid residues, located in close proximity, such as within a contiguous amino acid sequence, or located in distant parts of the amino acid sequence of an antigen, but due to protein folding have been approached to each other.

The invention concerns an epitope which comprises at least 3 amino acid residues selected
  1) from amino acid residues 83-90, 96-105, 137-150, 210-220, 304-314 and/or 318-329 of the SEQ ID NO: 1;
  2) consisting of a sequence selected from SEQ ID NOs: 2-7, or a fragment thereof, or
  3) comprising a combination of amino acid residues derived from any of the sequences of SEQ ID NOs: 2-7.

In a preferred embodiment the epitope is located in human YKL-40, is of 3 to 6 amino acid residues and comprises amino acid residues G, A, W, S, R, T and/or K.

Preferably, the invention concerns a monoclonal antibody against human YKL-40 characterized by a capability of recognising of and binding to the above epitope.

More particularly, the invention preferably concerns the group of functionally active mouse anti-human YKL-40 monoclonal antibodies identified herein as monoclonal antibodies 115F9, 116F9 and 201F9.

According to the invention antibodies 115F9, 116F9 and 201F9 are capable of binding to an epitope as defined above and thereby inhibiting the function of YKL-40 in connection with cell growth and survival by inhibiting at least one biological activity of YKL-40 protein described herein.

Functionally Active Antibody

Thus, the present invention relates to an antibody, an antigen binding fragment, or recombinant protein thereof, which is capable of recognising an epitope comprising or consisting of a sequence selected from any of the sequences identified as SEQ ID NOs: 2-7, of fragments thereof, said antibody, antigen binding fragment or recombinant protein being capable of modulating at least one biological activity of human YKL-40 or an YKL-40 functional homolog, or a functional fragment thereof, said activity being associated with i) cell growth ii) cell survival, iii) cell differentiation iv) extracellular matrix remodeling, v) development of liver fibrosis, vi) development of tissue fibrosis, vii) development of organ fibrosis, viii) development of angiogenesis, ix) development of rheumatoid arthritis, x) development of inflammation, and/or xi) development of metastasis.

In a preferred embodiment, the antibody is an anti-human YKL-40 monoclonal antibody.

The term "cell growth" is interchangeably used herein with the term "cell proliferation" and designates the phenomenon of great increase in cell number due to cell division.

The term "cell survival" is designate the phenomenon of cell continuing to live or exist, especially after coming close to dying or being destroyed, or after being improperly treated, for example as with factors affecting cell homeostasis so that inducing cell self destruction due to apoptosis. The wording "inhibition/stimulation cell survival" is interchangeably used herein with the wording "stimulation/inhibition of apoptosis/cell death"

In the present content by the wording "YKL-40 functional homolog" is meant a polypeptide
  comprising one of the immunogenic fragments of human YKL-40 defined above,
  capable of at least one of YKL-40 biological activities associated with cell growth, survival, differentiation, apoptosis, angiogenesis, extracellular matrix remodeling, development of metastasis, development of liver fibrosis, development of tissue fibrosis, development of organ fibrosis, development of rheumatoid arthritis and/or development of inflammation being recognizable by an antibody of the invention, preferably monoclonal antibody 115F9, 116F9 and/or 201F9.

In the present content by the term "modulating" is meant that an antibody, an antigen binding fragment, or recombinant protein thereof, is capable of enhancing or diminishing biological activity of human YKL-40, or a functional homolog thereof, or a biologically active fragment thereof. In preferred embodiment the invention features an antibody, antigen binding fragment, or recombinant protein thereof, which is capable of modulating of at least one biological activity of YKL-40, such as stimulating of cell proliferation, cell growth, cell differentiation, cell survival, modulation of adhesion and/or motility of cells. In a preferred embodiment the cells are tumor cells. The tumor cells are in preferred embodiment cancer cells or hematological malignant cells. The cancer cells may be from either primary or metastatic cancer.

By "primary cancer" is meant a group of tumor cells, which have acquired at least one characteristic feature of cancer cells, however have not yet invaded the neighbouring tissues and hold together in a tumor localized at the place of primary origin. By "metastatic cancer" is meant a group of tumor cells, which originate from the cells of a primary cancer, which have invaded the tissue surrounding said primary cancer, disseminated through the body, adhered at a new distant place and grown to a new tumor.

The examples of primary and metastatic cancers of the present invention include, but is not limited by carcinoma of the breast, colorectal, pancreas, stomach, GIST, hepatocellular, lung, small cell lung, ovarian, uterine, cervix, bladder, renal, prostate, testis, thyroid carcinoma, malignant melanoma, osteosarcoma, chondrosarcoma, myosarcoma, glioblastoma or other brain tumors, head/neck other gastrointestinal and germ cell tumors, and haematologic malignancies.

A functional antibody according to invention is capable of modulating proliferation, differentiation, and/or influencing cell survival of both primary and metastatic cancer cells, preferably inhibiting cell growth/proliferation/differentiation of said cells and/or inducing/stimulating apotosis/cell death of said cells. In other embodiments, functional antibodies of the invention are also capable of modulating proliferation, and/or influencing cell survival of non-cancer cells such as endothelial, fibroblast, synovial, chondrocyte, blood cells (e.g. monocytes/macrophages, neutrophils and precursors), hepatic stellate cells, vascular smooth muscle, epithelial cells, as a biological activity of human YKL-40 has previously been shown play an important role in stimulation of proliferation and survival of these cells. The example of such YKL-40 biological activity may be selected from, but not limited by capability of YKL-40 of
i) binding of chitin,
ii) binding of heparin,
iii) binding of heparan sulphate,
iv) binding of hyaluronan,
v) binding of long and/or short oligosaccharides,
vi) serving as a cellular growth factor,
vii) serving as a chemo-attractant for cells,
viii) interfering with the synthesis of hyaluronan,
ix) stimulating signal transduction pathways associated with cell survival,
x) stimulating differentiation,
xi) stimulating angiogenesis,
xii) stimulating fibrogenesis,
xiii) stimulating extracellular matrix remodelling and/or
xiv) stimulating inflammation.

Thus, a functionally active antibody of the invention, an antigen binding fragment-thereof, or recombinant protein thereof, which specifically recognises an epitope(s) described herein, is capable of modulating any of the above biological activity of YKL-40, preferably, any activity, which is associated with the processes influencing cell proliferation or survival.

Antibodies 115F9, 116F9 and 201F9 are the preferred functionally active antibodies of the invention capable of modulating any one of the YKL-40 activities described above, or two or more of the activities.

Peptide Fragments

An epitope of the invention may be represented by 3 to 6 amino acid residues of the SEQ ID NO: 1, said amino acid residues are preferably located in the areas of YKL-40 comprising amino acid residues 83-90, 96-105, 137-150, 210-220, 304-314 and/or 318-329 according to the sequence of SEQ ID NO: 1, wherein the preferred amino acid residues being G, A, W, S, R, T and/or K. The epitope may also be represented by a contiguous amino acid sequence derived from the sequence of SEQ ID NO: 1, such as a sequence selected from SEQ ID NOs: 2-7 or a fragment thereof.

Thus, one aspect of the invention concerns the epitope(s) comprising or consisting of at least one of the sequences identified below:

```
                                        (SEQ ID NO: 2)
        LKNRNPNL (SEQ ID NO: 3)
        VGGWN FGSQR (SEQ ID NO: 4)
        LAWLYPGRRDKQHF (SEQ ID NO: 5)
        GAWRGTTGHHS (SEQ ID NO: 6)
        RGATVHIRTLGQ.

(SEQ ID NO: 7)
        YATKGNQWVGY,
``` or a fragment thereof, or a variant thereof.

The above sequences according to the invention are immunogenic fragments of human YKL-40, and an epitope comprising or consisting of at least one of these sequences is recognized by a functional antibody of the invention of above. Thus, in one aspect the peptide fragments identified above may be used for raising a functional antibody of the invention.

In another aspect of the invention, the peptide fragments may be used as alternative ligands of the YKL-40 receptor capable of competing for the binding sites on the receptor with YKL-40 protein. Competitive binding of the peptide fragments to the YKL-40 receptor may attenuate the function of YKL-40 executed through the receptor binding and activation. Thus, the peptide fragments may be used as compounds for the inhibiting the functions of YKL-40 protein executed through the receptor binding. Preferably, the peptide fragments are to be used for inhibiting the function of YKL-40 associated with the processes of
i) stimulating of cell growth,
ii) stimulating of cell survival,
iii) stimulation of cell proliferation,
iv) stimulating of cell differentiation,
v) stimulating of extracellular matrix remodeling,
vi) stimulating of development of liver fibrosis,
vii) stimulating of development of organ fibrosis,
viii) stimulation of development of tissue fibrosis,
ix) stimulating of development of rheumatoid arthritis, x) stimulation of development of metastasis,
xi) stimulating of angiogenesis, and/or
xii) stimulation of inflammation.

In the present application the standard one-letter code for amino acid residues, as well as the standard three-letter code are applied. Abbreviations for amino acids are in accordance with the recommendations in the IUPAC-IUB Joint Commission on Biochemical Nomenclature Eur. J. Biochem, 1984, vol. 184, pp 9-37. Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a peptide of the invention exists as the free carboxylic acid, this may also be specified as "—OH". However, the C-terminal amino acid of a compound of the invention may be the amidated derivative, which is indicated as "—NH—". Where nothing else is stated the N-terminal amino acid of a polypeptide comprise a free amino-group, this may also be specified as "H—".

Where nothing else is specified amino acid can be selected from any amino acid, whether naturally occurring or not, such as alfa amino acids, beta amino acids, and/or gamma amino acids. Accordingly, the group comprises but are not limited to: Ala, Val, Leu, Ile, Pro, Phe, Tip, Met, Gly, Ser, Thr, Cys, Tyr, Asn, Gln, Asp, Glu, Lys, Arg, His Aib, Nal, Sar, Orn, Lysine analogues, DAP, DAPA and 4Hyp.

Basic amino acid residues are according to invention represented by the residues of amino acids Arg, Lys, and His, acidic amino acid residues--by the residues of amino acids Glu and Asp. Basic and amino acid residues constitute a group of charged amino acid residues. The group of hydrophobic amino acid residues is represented by the residues of amino acids Leu, Ile, Val, Phe, Trp, Tyr, and Met.

According to the invention modifications of the peptides may be performed, such as for example glycosylation and/or acetylation of the amino acids.

In one embodiment variants may be understood as exhibiting amino acid sequences gradually differing from the preferred predetermined sequence, as the number and scope of insertions, deletions and substitutions including conservative substitutions increase. This difference is measured as a reduction in homology between the predetermined sequence and the variant.

According to the invention a peptide sequence may have the length of 5 or more amino acid residues. The length of 6-8 amino acid residues is preferred, as the epitope/immunogenic fragment of the invention preferably comprises 6-8 amino acid residues. However, immunogenic fragments of the above sequences consisting of 3 to 7 amino acid residues such as for example 4, 5, or 6, are also within the scope of the invention.

The upper limit for the number of amino acid residues in a peptide fragment of the invention may vary. Thus, a peptide fragment comprising an immunogenic fragment of the invention may have the length up to 250 amino acid residues. For example it may comprise from 5 to 150 amino acid residues, such as 5 to 125, for example 5 to 100, such as 5 to 80, for example 5 to 65, 5 to 50, 5 to 30 or 5 to 20.

Thus, the invention also features peptide fragments comprising or consisting of 8 to 25 amino acid residues, such as 8 to 20, for example 8 to 15. In other embodiments the length of a peptide fragment may be from 10 to 25, such as 12 to 25, for example from 14 to 25, or it may be from 14 to 20 or from 14 to 18 amino acid residues. In some embodiments, a peptide fragment comprising the immunogenic sequence of the invention (any of SEQ ID NO: 2-7) may consists of more then 25 amino acid residues, such as from 26 to 50 amino acid residues, for example 28-30, 31-35, 36-40, 41-45 or 46-49 amino acid residues.

It is understood that all the above peptide fragments comprise or consists of a least one of the sequences selected from SEQ ID NO: 2-7, or a fragment or variant thereof.

A peptide fragment of the invention may comprise or consist of more than one immunogenic sequence of SEQ ID NOs: 2-7 or fragments or variants thereof. The peptide fragments may be formulated as monomers. This means that they may be represented by single copies of individual peptide sequences comprising the immunogenic sequence. A peptide fragment may also comprise or consist of more than one copy of the same sequence. Thus, the invention also relates to polymers of individual peptide sequences of the above. A polymer of a peptide sequence may be represented by a single peptide chain, wherein an individual peptide sequence is repeated two or more times in the chain, or it may be a molecule, wherein copies of individual peptide sequence are connected to each other via a linker group. Non-limited examples of such polymers may be dendrimeric polymers, wherein individual copies of a peptide sequence are attached to a core molecule, such as lysine.

A compound may comprise or consist of two or more different immunogenic sequences of the invention.

The peptide fragments comprising immunogenic sequences of the invention may comprise or consist of variants of said sequences.

"Variants of peptide sequences" means that the peptides may be modified, for example by substitution of one or more of the amino acid residues. Both L-amino acids and D-amino acids may be used. Other modification may comprise derivatives such as esters, sugars, etc. Examples are methyl and acetyl esters. Polymerisation such as repetitive sequences or attachment to various carriers are well-known in the art, e.g. lysine backbones, such as lysine dendrimers carrying 4 peptides, 8 peptides, 16 peptides, or 32 peptides. Other carriers may be protein moieties, such as bovine serum albumin (BSA), or lipophilic dendrimers, or micelle-like carriers formed by lipophilic derivatives, or starburst (star-like) carbon chain polymer conjugates, or ligand presenting assembly (LPA) based on derivatives of diethylaminomethane.

Variants of the peptide fragments according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Val, Leu, and Ile, and independently thereof, variants, or fragments thereof, wherein at least one valine (Val) of said variant, or fragments thereof is substituted with an amino acid selected from the group of amino acids consisting of Gly, Ala, Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at least one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gln, and independently thereof, variants, or fragments thereof, wherein at least one aspargine (Asn) of said variants, or fragments thereof is substituted with an amino acid selected from the group of amino acids consisting of Asp, Glu, and Gln, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Gln, Ser, Thr, and Tyr.

It thus follows from the above that the same functional equivalent of a peptide fragment, or fragment of said functional equivalent may comprise more than one conservative amino acid substitution from more than one group of conservative amino acids as defined herein above. The term "conservative amino acid substitution" is used synonymously herein with the term "homologous amino acid substitution". The groups of conservative amino acids are as the following:
P, A, G, S, T (neutral, weakly hydrophobic)
Q, N, E, D, B, Z (hydrophilic, acid amine)
H, K, R (hydrophilic, basic)
L, I, V, M, F, Y, W (hydrophobic, aromatic)
C (cross-link forming)

Conservative substitutions may be introduced in any position of a preferred predetermined peptide of the invention or fragment thereof. It may however also be desirable to introduce non-conservative substitutions, particularly, but not limited to, a non-conservative substitution in any one or more positions.

A non-conservative substitution leading to the formation of a functionally equivalent fragment of the peptide of the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions, which take various of the foregoing characteristics into consideration, are well known to those of skill in the art and include: arginine and lysine; glutamate and aspartate; serine and threonine; glutamine and asparagine; and valine, leucine and isoleucine.

The function of YKL-40 which is associated with the processes of
i) stimulation of cell growth, and/or
ii) stimulation of cell proliferation, and/or
iii) stimulation of cell survival, and/or
iv) stimulation of cell differentiation, and/or
v) stimulation of development of metastases, and/or
vi) stimulation of extracellular matrix remodeling, and/or
vii) stimulation of development of liver fibrosis, and/or
viii) stimulation of development of organ fibrosis, and/or
ix) stimulation of development of tissue fibrosis and/or
x) stimulation of development of rheumatoid arthritis, and/or
xi) stimulation of angiogenesis, and/or
xii) stimulation of inflammation
may by selected from the following biological activities of YKL-40
i) binding of chitin, and/or
ii) binding of heparin, and/or
iii) binding of heparin sulphate and/or
iv) binding of hyaluronan, and/or
v) binding of long and/or short oligosaccharides, and/or
vi) serving as a cellular growth factor, and/or
vii) serving as a cellular differentiation factor, and/or
viii) serving as a chemo-attractant for cells, and/or
ix) interfering with the synthesis of hyaluronan, and/or
x) interfering with extracellular matrix remodeling and/or
xi) stimulating signal transduction pathways associated with cell survival, and/or
xii) stimulating angiogenesis, and/or
xiii) interfering with inflammation, and/or
xiv) stimulating fibrogenesis.

These biological functions of YKL-40 are according to the invention executed involving the structural areas of the protein, which comprise or consist of at least one of the following sequences

```
                                            (SEQ ID NO: 2)
         \LKNRNPNL (SEQ ID NO: 3)
         VGGWN FGSQR (SEQ ID NO: 4)
         LAWLYPGRRDKQHF (SEQ ID NO: 5)
         GAWRGTTGHHS (SEQ ID NO: 6)
         RGATVHRTLGQ.

(SEQ ID NO: 7)
         YATKGNQWVGY
```

According to the invention, the SEQ ID NOs: 2-7 all or at least one of them are involved in formation of a receptor binding site on YKL-40, said site being involved in execution at least one of the above identified biological activities of YKL-40. Therefore, the invention considers the presence any of the sequences of SEQ ID NOs: 2-7 in a longer peptide sequence to be essential for said longer peptide sequence possesses the capability to competitive (i) binding to the YKL-40 receptor, and/or (ii) binding to the functionally active antibody of the invention. Thus, a sequence which includes at least one of the sequences of SEQ ID NOs: 2-7 is concerned by the invention as a modulator of biological activity of human YKL-40 in vivo and in vitro. Thus, when such sequence competes with YKL-40 for the receptor binding, the sequence may thereby attenuate the activity of YKL-40, such as down-regulate stimulation of cell proliferation, differentiation and/or cell survival induced by YKL-40, or when compete for the antibody binding, the sequence may attenuate the inhibiting activity of the antibody and thereby up-regulate stimulation of cell proliferation and/or cell survival dependent on YKL-40. Accordingly, a peptide sequence of 8-200 amino acids long comprising a sequence selected for SEQ ID NOs: 2-7, or a fragment thereof, or a variant thereof, is considered to be a functional homologue of human YKL-40, or functional homologue any of the sequences identified as SEQ ID NOs: 2-7.

Production of Individual Peptide Sequences

The peptide sequences of the present invention may be prepared by any conventional synthetic methods, recombinant DNA technologies, enzymatic cleavage of full-length proteins which the peptide sequences are derived from, or a combination of said methods.

Recombinant Preparation

Thus, in one embodiment the peptides of the invention are produced by use of recombinant DNA technologies.

The DNA sequence encoding a peptide or the corresponding full-length protein the peptide originates from may be prepared synthetically by established standard methods, e.g. the phosphoamidine method described by Beaucage and Caruthers, 1981, Tetrahedron Lett. 22:1859-1869, or the method described by Matthes et al., 1984, EMBO J. 3:801-805. According to the phosphoamidine method, oligonucleotides are synthesised, e.g. in an automatic DNA synthesiser, purified, annealed, ligated and cloned in suitable vectors.

The DNA sequence encoding a peptide may also be prepared by fragmentation of the DNA sequences encoding the corresponding full-length protein of peptide origin, using DNAase I according to a standard protocol (Sambrook et al., Molecular cloning: A Laboratory manual. 2 rd ed., CSHL Press, Cold Spring Harbor, N.Y., 1989). The present invention relates to full-length proteins selected from the groups of proteins identified above. The DNA encoding the full-length proteins of the invention may alternatively be fragmented using specific restriction endonucleases. The fragments of DNA are further purified using standard procedures described in Sambrook et al., Molecular Cloning: A Laboratory Manual, 2nd Ed., CSHL Press, Cold Spring Harbor, N.Y., 1989.

The DNA sequence encoding a full-length protein may also be of genomic or cDNA origin, for instance obtained by preparing a genomic or cDNA library and screening for DNA sequences coding for all or part of the full-length protein by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al., 1988, Science 239:487-491.

The DNA sequence is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding a peptide or a full-length protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter (Subramani et al., 1981, Mol. Cell. Biol. 1:854-864), the MT-1 (metallothionein gene) promoter (Palmiter et al., 1983, Science 222: 809-814) or the adenovirus 2 major late promoter. A suitable promoter for use in insect cells is the polyhedrin promoter (Vasuvedan et al., 1992, FEBS Left. 311:7-11). Suitable promoters for use in yeast host cells include promoters from yeast glycolytic genes (Hitzeman et al., 1980, J. Biol. Chem. 255:12073-12080; Alber and Kawasaki, 1982, J. Mol. Appl. Gen. 1: 419-434) or alcohol dehydrogenase genes (Young et al., 1982, in Genetic Engineering of Microorganisms for Chemicals, Hollaender et al, eds., Plenum Press, New York), or the TPI1 (U.S. Pat. No. 4,599,311) or ADH2-4c (Russell et al., 1983, Nature 304: 652-654) promoters. Suitable promoters for use in filamentous fungus host cells are, for instance, the ADH3 promoter (McKnight et al., 1985, EMBO J. 4:2093-2099) or the tpiA promoter.

The coding DNA sequence may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 EIb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op. cit.).

To obtain recombinant peptides of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-5-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or Acharombacter lyticus, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. Xenopus laevis oocytes or mammalian cells, in particular insect and mammalian cells. Examples of suitable mammalian cell lines are the HEK293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are described in e.g. Kaufman and Sharp, J. Mol. Biol. 159, 1982, pp. 601-621; Southern and Berg, 1982, J. Mol. Appl. Genet. 1:327-341; Loyter et al., 1982, Proc. Natl. Acad. Sci. USA 79: 422-426; Wigler et al., 1978, Cell 14:725; Corsaro and Pearson, 1981, in Somatic Cell Genetics 7, p. 603; Graham and van der Eb, 1973, Virol. 52:456; and Neumann et al., 1982, EMBO J. 1:841-845.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g. in catalogues of the American Type Culture Collection).

The peptides or full-length proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

Synthetic Preparation

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

Peptides may for example be synthesised by using Fmoc chemistry and with Acm-protected cysteins. After purification by reversed phase HPLC, peptides may be further processed to obtain for example cyclic or C- or N-terminal modified isoforms. The methods for cyclization and terminal modification are well-known in the art and described in detail in the above-cited manuals.

In a preferred embodiment the peptide sequences of the invention are produced synthetically, in particular, by the Sequence Assisted Peptide Synthesis (SAPS) method.

By SAPS peptides may be synthesised either batchwise in a polyethylene vessel equipped with a polypropylene filter for filtration or in the continuous-flow version of the polyamide solid-phase method (Dryland, A. and Sheppard, R. C., (1986) J. Chem. Soc. Perkin Trans. I, 125-137.) on a fully automated peptide synthesiser using 9-fluorenylmethyloxycarbonyl (Fmoc) or tert.-Butyloxycarbonyl, (Boc) as N-a-amino protecting group and suitable common protection groups for side-chain functionality. When synthesised, individual peptide sequences may then be formulated as multimers using well-known in the art techniques, for examples dimers of the sequences may be obtained by the LPA method described in WO 00/18791, denrimeric polymers by the MAP synthesis are described in PCT/US90/02039.

Pharmaceutical Composition

In the present context the term "pharmaceutical composition" is used synonymously with the term "medicament".

In some embodiments the invention concerns a pharmaceutical composition comprising an antibody capable of binding the epitope as defined above, antigen binding fragment or recombinant protein thereof. Preferably, a pharmaceutical composition comprises monoclonal antibodies 115F9, 116F9 and/or 201F9, antigen binding fragment or recombinant protein thereof, most preferably monoclonal antibody 201F9, antigen binding fragment or recombinant protein thereof. Most preferably, a pharmaceutical composition of the invention comprises or essentially comprises a humanized form(s) of antibodies 115F9, 116F9 and/or 201F9.

In other embodiments the invention concerns a pharmaceutical composition comprising an immunogenic fragment of YKL-40, said fragment comprising at least one of the sequences identified as SEQ ID NOs: 2-7.

In one embodiment a pharmaceutical composition comprises the peptide sequence identified as SEQ ID NO: 2, or a fragment thereof, or a variant thereof. In another embodiment the composition comprises the peptide sequence identified as SEQ ID NO: 3, or a fragment thereof, or a variant thereof. In still another embodiment the composition comprises the peptide sequence identified as SEQ ID NO: 4, or a fragment thereof, or a variant thereof. In yet another embodiment the composition comprises the peptide sequence identified as SEQ ID NO: 5, or a fragment thereof, or a variant thereof. In still yet another embodiment the composition comprises the peptide sequence identified as SEQ ID NO: 6, or a fragment thereof, or a variant thereof, or the peptide sequence identified as SEQ ID NO: 6, or a fragment thereof, or a variant thereof. In some embodiments a pharmaceutical composition may comprise any combination of the sequences SEQ ID NOs.: 2-7.

In a composition the peptide sequences may be formulated as isolated individual peptide fragments or multimers or dimers thereof as discussed above.

The pharmaceutical composition described above may for example be used to promote death of cancer cells in vitro or in vivo.

The composition is administered to a subject in vivo or to be used in vitro contains an effective amount of one or more of the compounds described above in combination with pharmaceutically acceptable additives. Such medicament may suitably be formulated for oral, percutaneous, intramuscular, intravenous, intracranial, intrathecal, intracerebroventricular, intranasal or pulmonal administration.

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred µg active ingredient per administration with a preferred range of from about 0.1 µg to 5000 µg per kilo body weight. Using monomeric forms of the compounds, the suitable dosages are often in the range of from 0.1 µg to 5000 µg per kilo body weight, such as in the range of from about 0.1 µg to 3000 µg per kilo body weight, and especially in the range of from about 0.1 µg to 1000 µg per kilo body weight. Using multimeric forms of the compounds, the suitable dosages are often in the range of from 0.1 µg to 1000 µg per kilo body weight, such as in the range of from about 0.1 µg to 750 µg per kilo body weight, and especially in the range of from about 0.1 µg to 500 µg per kilo body weight such as in the range of from about 0.1 µg to 250 µg per kilo body weight. In particular when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For some indications a localised or substantially localised application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promotes delivery of the active substance to its target.

In many instances, it will be necessary to administrate the formulation multiple times. Administration may be a continuous infusion, such as intraventricular infusion or administration in more doses such as more times a day, daily, more times a week, weekly, etc. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

In connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

The present invention also relates to treatment of individuals in need for inducing cell death, inhibiting cell growth development of liver fibrosis or rheumatoid arthritis. The treatment involves administering an pharmaceutical composition of the invention comprising an effective amount of one or more compounds as defined above.

Treatment

As discussed above, antibodies and peptide fragments described herein may be used for modulating, such as inhibiting or stimulating, a least one of YKL-40 biological activities listed below:
i) binding of chitin,
ii) binding of heparin,
iii) binding of heparan sulphate,
iv) binding of hyaluronan,
v) binding of long and/or short oligosaccharides,
vi) serving as a cellular growth factor,
vii) serving as a differentiation factor,
viii) serving as a chemo-attractant for cells,
ix) interfering with the synthesis of hyaluronan,
x) stimulating signal transduction pathways associated with cell survival, xi) stimulating angiogenesis,
xii) stimulating fibrogenesis,
xiii) interfering with extracellular matrix remodeling,
xiv) interfering with inflammation, and/or
xv) stimulating development of metastasis The above activities of human YKL-40 have been associated with the capability of the protein to stimulate cell growth, proliferation, differentiation and survival, extracellular matrix remodeling, fibrosis and angiogenesis. Therefore, antibodies and peptide fragments of the invention may also be used for inhibiting cell growth, proliferation, differentiation and survival, development of metastases and/or extracellular matrix remodeling, fibrosis, angiogenesis and inflammation. There is a number of diseases and pathological conditions wherein treatment of an individual in need comprising using such antibodies and/or peptide fragments, or a pharmaceutical composition comprising thereof may lead to successful curing. The term "antibody" in the present context designates both antibodies, antigen binding fragments and recombinant proteins thereof.

Thus, the antibodies and/or peptide fragments, or a pharmaceutical composition comprising thereof may successfully be used for the treating any primary cancer selected from breast-, colorectal-, pancreas-, stomach-, hepatocellular-, other gastrointestinal-, lung-, small cell lung-, ovarian-, uterine-, cervix-, testis-, prostate, bladder-, renal-, thyroid- and head/neck carcinoma, malignant melanoma and other skin cancers, osteosarcoma, chondrosarcoma, myosarcoma, glioblastoma or other brain tumors, germ cell tumors and haematopoietic malignancies.

Or, the antibody and/or peptide fragments, or a pharmaceutical composition comprising thereof may be used for the treating any metastatic cancer selected from breast-, colorectal-, pancreas-, stomach-, hepatocellular-, other gastrointestinal-, lung-, small cell lung-, ovarian-, uterine-, cervix-, testis-, prostate, bladder-, renal-, thyroid- and head/neck carcinoma, malignant melanoma and other skin cancers, osteosarcoma, chondrosarcoma, myosarcoma, glioblastoma or other brain tumors, germ cell tumors and haematopoietic malignancies.

Yet, in another embodiment, the antibody and/or peptide fragments, or a pharmaceutical composition comprising thereof may be used for the treating an inflammatory disease selected from e.g. rheumatoid arthritis, other inflammatory joint diseases, bacterial infection, active inflammatory bowel disease or liver fibrosis (e.g. caused by hepatitis B or C virus or alcohol abuse).

Still, in other embodiments, the antibody, and/or peptide fragments, or a pharmaceutical composition comprising thereof may also be used for the
  inhibiting proliferation of any non-tumor cells;
  inhibiting angiogenesis;
  inhibiting extracellular matrix remodelling;
  inhibiting of tissue fibrosis, at any pathological condition, such as for example rheumatoid arthritis, giant cell arteritis, ankylosing spondylitis, tuberculosis, sarcoidosis, scleroderma, Crohns disease, ulcerative colitis, alcoholic liver fibrosis, hepatitis C wherein said inhibition may be advantageous for curing.

In yet a further aspect the invention relates to a method of treating a disease or condition as discussed above by administering the antibody and/or peptide fragments of the invention, or a pharmaceutical composition comprising thereof.

Additionally, the invention concerns using antibodies and/or peptide fragments of the invention, or a pharmaceutical composition comprising thereof in in vitro assays and methods, for example in assays for screening new anti-cancer compounds.

EXAMPLES

1. Inhibition of Cancer Cell Growth and Survival by Anti-Human YKL-40 Monoclonal Antibodies In Vitro Cells of human malignant glioblastoma U87, human osteosarcomas MG63 and U2OS, and human malignant melanoma SK-MEL28 were routinely maintained in culture in Dulbecco's modified Eagle's medium (DMEM) (Gibco), supplemented with 10% foetal calf serum (FCS) and antibiotics (penicillin and streptomycin). All cell lines were obtained from ATTC.
Anti-Human YKL-40 Antibodies (Ab):
116F9 (mouse monoclonal; highest Ab dilution 1:100 is equal to Ab concentration 0.06 mg/ml
115F9 (mouse monoclonal; highest Ab dilution 1:50 is equal to Ab concentration 0.03 mg/ml)
201F9 (mouse monoclonal; highest Ab dilution 1:250 is equal to Ab concentration 0.03 mg/ml)
R668 (rabbit polyclonal; highest Ab dilution 1:50 is equal to Ab concentration 0.0075 mg/ml)
Procedure:
Cells were seeded in 96-well plates (12 wells×8 rows) with a density of 5000 cells/well in 200 µl media. The cells were allowed to attach and grow overnight. Next day the growth media was discarded and cells were rinsed with phosphate buffered saline (PBS). Subsequently, cells were treated with 200% fresh media containing different dilutions of the antibodies as shown below:
TABLE-US-00003 Plate 1+2 Plate 3+4 Plate 5+6 Plate 7+8 Row 115F9 116F9 201F9 R667 1 A: Negative Negative Negative Negative 2 B: 1:50 Negative Negative 1:50 3 C: 1:100 1:100 Negative 1:100 4 D: 1:250 1:250 1:250 1:250 5 E: 1:500 1:500 1:500 1:500 6 F: 1:1000 1:1000 1:1000 1:1000 7 G: 1:2500 1:2500 1:2500 1:2500 8 H: 1:5000 1:5000 1:5000 1:5000

On each plate wells 1 to 6 of each row were incubated in the presence of 10% FCS in the media, wells 7 to 12 were incubated in the presence of 0.1% bovine serum albumine (BSA) without FCS in the media.

One plate of each antibody treatment was incubated at normoxia conditions, and another plate at hypoxia (0.1%) conditions for 72 hours before treatment with MTT (3-(4,5-dimethylthiazol-2-yl)-2,5-diphenyl tetrazolium bromide, Sigma).
MTT Assay:
MTT-assay (allows to distinguish between living and dead cells in the culture) was performed according to Mossmann T. J Immunol Methods 65:55-63, 1983.

40 µl MTT was added to each well (2 mg/ml stock solution) and the plates were incubated for 1 hour at 37° C. in a normoxic incubator. Afterwards the media was discarded and 100 .mu.l DMSO added to each well. Plates were shaken for 10 sec and the OD (optical density) values were read at 570 nm (with the background correction on 690 nm). Results are given as an average of OD in 6 wells+/−standard deviation.

Figure 2:
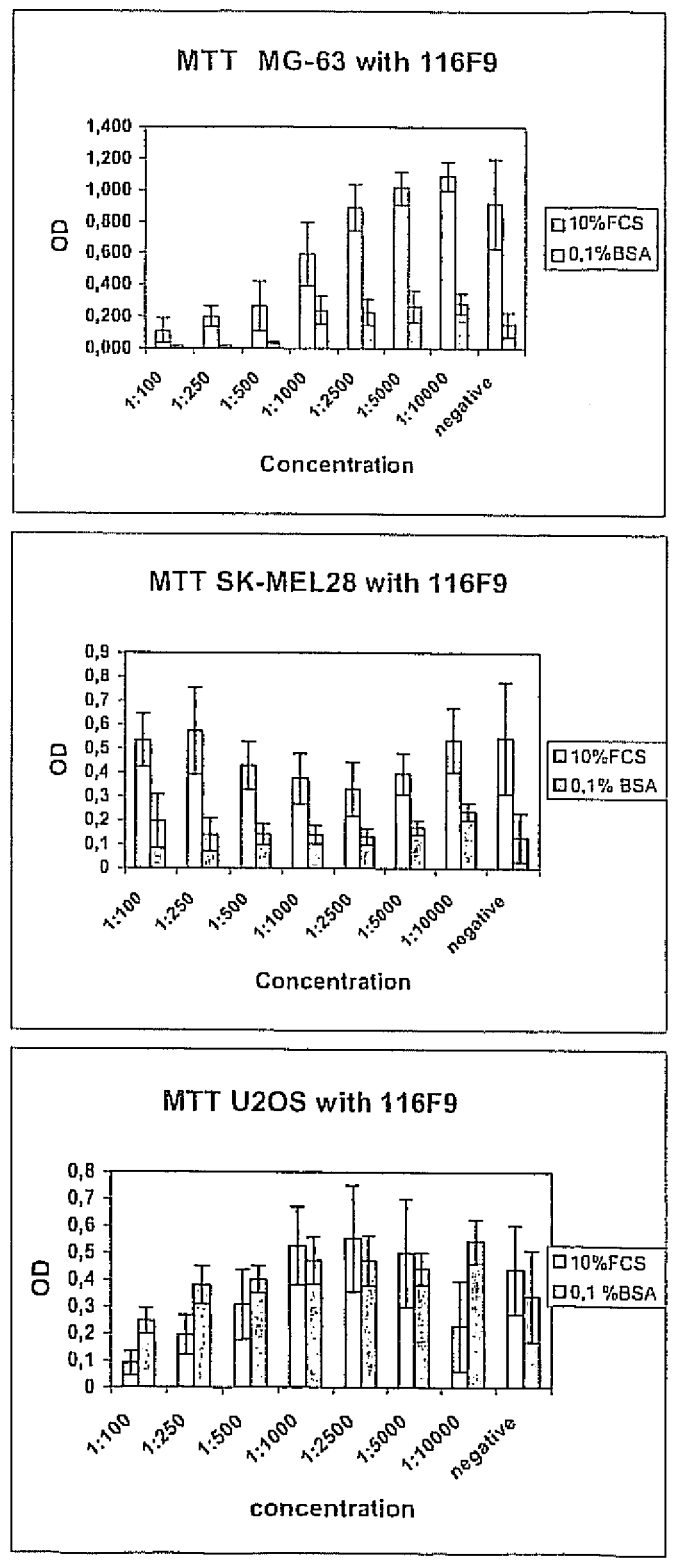
FIG. 2 demonstrates the inhibiting effect of mAb 116F9 on cell growth and survival of human osteosarcoma cells U2OS and MG-63 and human malignant melanoma cells SK-MEL-28 in vitro (MTT assay). Results are given as the mean value of 6 measurements+/−standard deviation.

As it can been seen from FIG. 1 monoclonal antibodies (MAb) 116F9 and 201F9 have a repressive effect on growth of U87 glioblastoma cells reflected by a reduced number of cells in treated wells (with antibody) compared to control wells (without antibody named "Kontrol" in FIG. 1 and "Negative" in FIG. 2) after 72 hours of treatment independently of the presence FCS in the culture media. Monoclonal Ab 115F9 and polyclonal Ab R667 (not shown) did not inhibit the growth of tested cancer cells. MAb116F9 was further tested in cultures of two human osteosarcoma cell lines MG63 and U2OS and one human malignant melanoma cell line SK-MEL-28. The results shown in FIG. 2 demonstrate that MAb 116F9 has a growth repressive effect in both osteosarcoma cells, but not in melanoma SK-MEL-28 cells. The two tested osteosarcoma cell lines are characterized by a high expression level of YKL-40, whereas SK-MEL-28 cells line has a very low expression level, if any.

These results demonstrate that monoclonal antibodies against YKL-40 (MAb 116F9 and 201F9) have the growth repressive effect in YKL-40 expressing cancer cells. The effect may be due to inhibition of cell growth and survival or induction of apoptosis, or due to both.

Example 2

Figure 3:
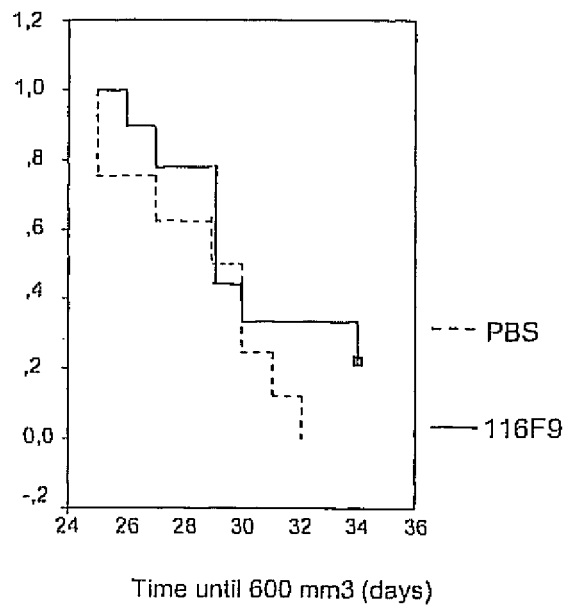
FIG. 3 shows the Kaplan-Meier plots of the growth of individual tumors (days until tumor size 600 mm$^3$) in nude mice injected with human glioblastoma cells U87 and treated with monoclonal antibody (MAb) 201F9, 116F9 or phosphate buffered saline (PBS) (control).
Figure 3:
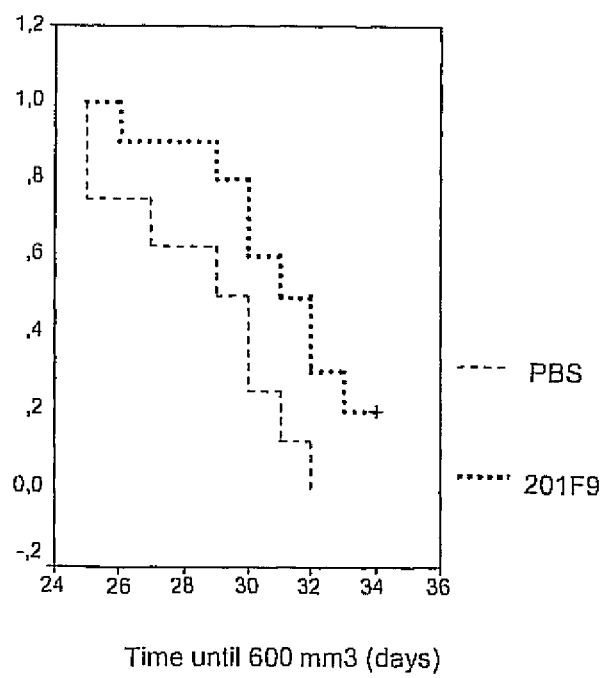

Inhibition of Cancer Cell Growth by Anti Human YKL-40 Monoclonal Antibodies In Vivo Human glioblastoma U87 cells ($4 \times 10^6$ cells/tumor) were injected subcutaneous in nude mice. When tumors reached an average volume of 100 mm$^3$, the mice were divided in 3 groups of ten mice each. Group A were treated with 40 mg/kg MAb 201F9 i.p. from treatment day 1 and twice a week hereafter. Group B were treated with 28 mg/kg MAb 116F9 i.p. from treatment day 1 and twice a week hereafter. Group C (control) received PBS (phosphate buffered NaCl) i.p. twice weekly. Tumor size was measured daily and the mice were sacrificed when tumor size reached the volume of 1000 mm$^3$. Effect of the treatments on the growth of individual tumors until 600 mm$^3$ is shown in FIG. 3 (Kaplain-Meier curves). It can be seen that twice-weekly injections of MAb 201F9 (40 mg/kg) reduces growth of U87 tumors compared to tumors in PBS treated animals (Log rank test p<0.05). This is the case for two different time terms of treatment—the days until the tumor is reached the volume of 600 mm$^3$ and the days to the volume of 900 mm$^3$ (not shown). FIG. 3 shows that MAb 116F9 had no significant inhibiting effect on growth of U87 tumors compared to growth of the tumors in PBS treated nude mice. However, mice treated with 116F9 received a lower dose of the antibody compared to mice treated with antibody 201F9, and one could speculate that 116F9 given at a higher dose might have an inhibiting effect on tumor growth.

In another experiment human glioblastoma U87 cells ($8 \times 10^6$ cells/tumor) were injected subcutaneous in nude mice. When tumors reached an average volume of 200 mm$^3$, the mice were divided in 4 groups of ten mice each. Group A and C received 8 Gy of ionising radiation (IR) at treatment day 1. Group A and B were treated with 40 mg/kg MAb 201F9 i.p. from treatment day 1 and twice a week hereafter. Group D (control) received PBS (phosphate buffered NaCl) i.p. twice weekly. Tumor size was measured daily and the mice were sacrificed when tumor size reached the volume of 1000 mm$^3$. Effect of the treatments on the growth of tumors until 600 mm$^3$ is shown in FIG. 4.

Figure 4:
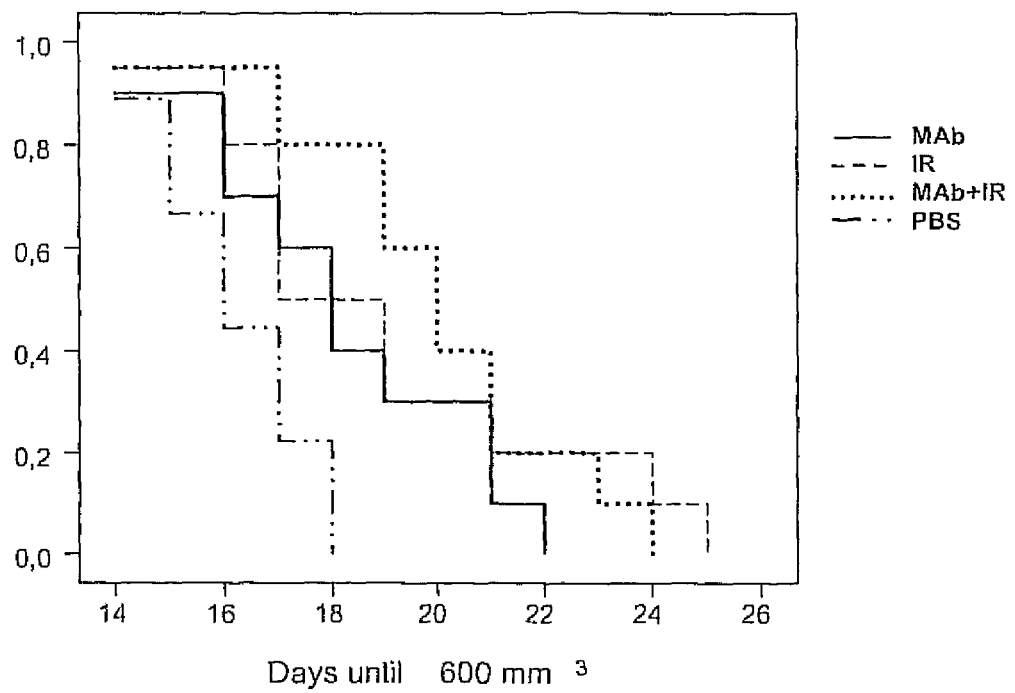
FIG. 4 presents the Kaplan Meier plots of the growth of individual tumors (days until tumor size 600 mm$^3$) in nude mice injected with human glioblastoma cells U87 and treated with ionizing radiation (IR), monoclonal antibody 201F9 (MAb), simultaneously with ionizing radiation and monoclonal antibody 201F9 (IR+MAb) or phosphate buffered saline (PBS) (control). Ten mice in each group.

Results demonstrated in FIG. 4 show that ionizing radiation (IR) has also a significant growth reducing effect on the tumors, which is comparable to the effect of the antibody MAb 201F). Simultaneous treatment with MAb 201F9 and IR does not lead to a synergetic effect of Mab and IR. The P-values for log-rank test are summarized in table 1 below:

|  | T600 | T900 |
|---|---|---|
| PBS v. MAb | P = 0.0465 | P = 0.0472 |
| PBS v. IR | P = 0.021 | P = 0.0067 |
| IR v. IR + MAb | P = 0.877 | P = 0.8235 |

P—values are Log-rank test.
IR—ionizing radiation
MAb—monoclonal Ab 201F9
T600—period of time until the volume of tumor grown to 600 mm$^3$
T900—period of time until the volume of tumor grown to 900 mm$^3$

Example 3

YKL-40 Epitope Mapping for mAb 201F9

The epitope mapping was performed by analysing binding of antibody 201F9 to peptide fragments of human YKL-40 (Swissprot As. No.: P36222; SEQ ID NO: 1). A peptide library of 381 overlapping peptide fragments (of 8-14 amino acid residues) of YKL-40 sequence was synthesized and screened for a capability of binding to 201F9 Ab by Pepscan Systems BV (The Netherlands)

Several groups of the peptides covering the areas of YKL-40 comprising amino acid residues 81-105, 127-165, 203-223, 279-292, 300-316 and 318-335 demonstrated significant binding. Based on these data and analysis of structural areas of YKL-40, which include these peptide fragments, a new group of peptides was designed, synthesized and screened for antibody binding. The new peptides were designed considering the position of a peptide sequence in a loop structure of the YKL-40 protein to be favourable.

Figure 5:
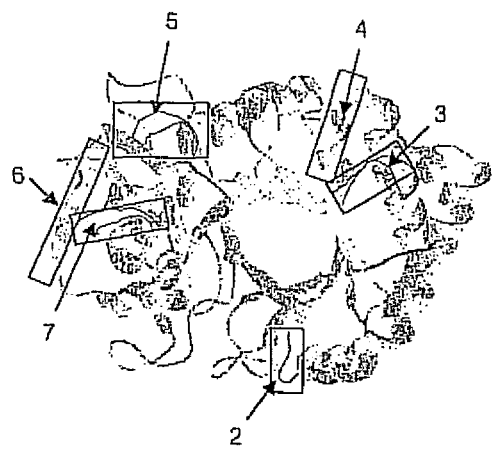
FIG. 5 shows a schematic presentation of localization of peptide sequences comprising the epitope for Mab 201F9 (SEQ ID NOs: 2-7) in the 3D structure of YKL-40.

Six peptides covering residues 83-90 (SEQ ID NO: 2), 96-105 (SEQ ID NO: 3), 137-150 (SEQ ID NO: 4), 210-220 (SEQ ID NO: 5), 304-314 (SEQ ID NO: 6), and 318-329 (SEQ ID NO: 7) were identified as possible antigenic determinants/epitopes for antibody 201F9. FIG. 5 demonstrates the location of the peptides in the structure of YKL-40. The sequences of the peptide fragments were aligned and it appeared that the sequences of SEQ ID NOs: 2, 3, 4, 5, 6 and 7 share homology. In table 2 (below) the sequences are aligned and homology of amino acid residues is shown in bold indicating the identical amino acid residue and bold underlined—the homologous amino acid residue.

TABLE 2

| |
|---|
| GAWRGTTGHHS (SEQ ID NO: 5) |
| YATKGNQWVGY (SEQ ID NO: 7) |
| GAWRGTTGHHS (SEQ ID NO: 5) |
| RGATVHRTLGQ (SEQ ID NO: 6) |
| GAWRGTTGHHS (SEQ ID NO: 5) |
| LAWLYPGRRDKQHF (SEQ ID NO: 4) |
| GAWRGTTGHHS (SEQ ID NO: 5) |
| VGGWN FGSQR (SEQ ID NO: 3) |
| GAWRGTTGHHS (SEQ ID NO: 5) |
| LKNRNPNL (SEQ ID NO: 2) |

From the table it appears that residues G, A, W, R, T, P and S are most probably the residues that determine antigenic properties of the sequences, and sequence GAWRGTTGHHS (SEQ ID NO: 5) is likely the sequence that comprises the major epitope for antibody 201F9.

Amino acid residues located within the sequences corresponding to residues 210-220 (SEQ ID NO: 5) and 137-150 (SEQ ID NO: 4) of YKL-40 have previously been shown involved in YKL-40-ligand/receptor binding (see for example Houston et al. (2003) J Biol Chem 278:30206-30212, and Fusetti et al. (2003) J Biol Chem 278:37753-37760). The present data demonstrate that the sequences also comprise antigenic determinates for antibody 201F9. Occupation of these residues by the antibody inhibits biological activity of YKL-40 and therefore leads to the inhibition of growth of cancer cells.

The invention claimed is:

1. A method of inhibiting cancer cell growth, said method comprising contacting said cancer cell with a monoclonal antibody, antigen binding fragment or recombinant protein thereof, which is specific for human YKL40 (SEQ ID NO: 1), said antibody, binding fragment or recombinant protein thereof being capable of inhibiting growth of a cancer cell upon binding to an epitope on YKL-40.

2. The method according to claim 1, wherein said antibody, antigen binding fragment or recombinant protein is capable of specifically recognizing and binding to an epitope consisting of residues 210-220 of SEQ ID NO: 1.

3. The method according to claim 1, wherein the antibody is an immunoglobulin selected from the group consisting of IgA, IgD, IgE, IgG and IgM.

4. The method according to claim 1, wherein the antibody is capable of inhibiting growth of a cell upon binding to an epitope on YKL-40, wherein the cell is selected from the group consisting of U87, MG63 and U2OS.

5. The method according to claim 1, wherein the method is a method of treating cancer in an individual in need thereof.

6. An antibody, antigen binding fragment or recombinant protein thereof, which is specific for human YKL40 (SEQ ID NO: 1), said antibody, binding fragment or recombinant protein thereof being capable of inhibiting growth of a cancer cell upon binding to an epitope on YKL-40, wherein said antibody, antigen binding fragment or recombinant protein, is capable of specifically recognizing and binding to an epitope consisting of residues 83-90, 96-105, 137-150, 210-220, 304-314 and/or 318-329 of the sequence of human YKL-40 identified as SEQ ID NO: 1.

7. The antibody according to claim 6, wherein the antibody is a monoclonal antibody.

* * * * *

```
                        SEQUENCE LISTING

<160> NUMBER OF SEQ ID NOS: 7

<210> SEQ ID NO 1
<211> LENGTH: 383
<212> TYPE: PRT
<213> ORGANISM: Homo sapiens

<400> SEQUENCE: 1

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
                20                  25                  30

Gln Tyr Arg Glu Gly Asp Gly Ser Cys Phe Pro Asp Ala Leu Asp Arg
            35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
    290                 295                 300
```

```
Gly Ala Thr Val His Arg Thr Leu Gly Gln Gln Val Pro Tyr Ala Thr
305                 310                 315                 320

Lys Gly Asn Gln Trp Val Gly Tyr Asp Asp Gln Glu Ser Val Lys Ser
            325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380

<210> SEQ ID NO 2
<211> LENGTH: 8
<212> TYPE: PRT
<213> ORGANISM: Artificial Sequence
<220> FEATURE:
<223> OTHER INFORMATION: peptide fragment of YKL-40

<400> SEQUENCE: 2

Leu Lys Asn Arg Asn Pro Asn Leu
1               5

<210> SEQ ID NO 3
<211> LENGTH: 10
<212> TYPE: PRT
<213> ORGANISM: Artificial Sequence
<220> FEATURE:
<223> OTHER INFORMATION: peptide fragment of YKL-40

<400> SEQUENCE: 3

Val Gly Gly Trp Asn Phe Gly Ser Gln Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: peptide fragment of YKL-40

<400> SEQUENCE: 4

Leu Ala Trp Leu Tyr Pro Gly Arg Arg Asp Lys Gln His Phe
1               5                   10

<210> SEQ ID NO 5
<211> LENGTH: 11
<212> TYPE: PRT
<213> ORGANISM: Artificial Sequence
<220> FEATURE:
<223> OTHER INFORMATION: peptide fragment of YKL-40

<400> SEQUENCE: 5

Gly Ala Trp Arg Gly Thr Thr Gly His His Ser
1               5                   10

<210> SEQ ID NO 6
<211> LENGTH: 11
<212> TYPE: PRT
<213> ORGANISM: Artificial Sequence
<220> FEATURE:
<223> OTHER INFORMATION: peptide fragment of YKL-40

<400> SEQUENCE: 6

Arg Gly Ala Thr Val His Arg Thr Leu Gly Gln
1               5                   10
```

```
<210> SEQ ID NO 7
<211> LENGTH: 11
<212> TYPE: PRT
<213> ORGANISM: Artificial Sequence
<220> FEATURE:
<223> OTHER INFORMATION: peptide fragment of YKL-40

<400> SEQUENCE: 7

Tyr Ala Thr Lys Gly Asn Gln Trp Val Gly Tyr
1               5                   10
```